United States Patent [19]
Trost et al.

[11] Patent Number: 6,130,349
[45] Date of Patent: Oct. 10, 2000

[54] CATALYTIC COMPOSITIONS AND METHODS FOR ASYMMETRIC ALLYLIC ALKYLATION

[75] Inventors: Barry M. Trost, Los Altos, Calif.; Iwao Hachiya, Tokyo, Japan

[73] Assignee: The Board of Trustees of the Leland Stanford Junior University, Stanford, Calif.

[21] Appl. No.: 09/213,395

[22] Filed: Dec. 15, 1998

Related U.S. Application Data

[60] Provisional application No. 60/068,128, Dec. 19, 1997.

[51] Int. Cl.$^7$ .................. C07C 69/76; C07C 233/02; C07F 213/02; C07F 307/02; C07D 207/02

[52] U.S. Cl. .................. 560/100; 564/167; 546/2; 546/341; 540/484; 548/402; 549/206; 549/346; 560/103; 560/104; 560/205

[58] Field of Search .................. 540/484; 546/2; 546/341; 548/402; 549/206, 346; 560/103, 104, 205, 100; 564/167

[56] References Cited

PUBLICATIONS

J. Am. Chem. Society 1990 vol. 112 pp. 9590–9600 Barry Trost et al, Apr. 2, 1990.

Agnew. Chem. Int. Ed. Engl. 1995. vol. 34. No. 4, Sep. 1, 1994.

Dvořák, D., et al., "Stereochemistry of Molybdenum (0)–Catalyzed Allylic Substitution: The First Observation of a Syn–Syn Mechanism," *J. Am. Chem. Soc. 117*:6130–6131 (1995).

Faller, J.W., and Linebarrier, D., "Reversal of Stereochemical Path in Allylic Alkylations Promoted by Palladium and Molybdenum Complexes," *Organometallics 7*:1670–1672 (1988).

Lloyd–Jones, G.C., and Pfaltz, A., "Chiral Phosphanodihydro–oxazoles in Asymmetric Catalysis: Tungsten–Catalyzed Allylic Substitution," *Angew. Chem. Int. Ed. Engl. 34*(4):462–464 (1995).

Rubio, A., and Liebeskind, L.S., "Enantiospecific Synthesis by Transformations of Chiral Pool–Derived Metal α–Complexes. A Strategy for the Introduction of Substituents on a Pyranose–Derived Lateral α–Ligand either Syn or Anti to the Coordinating Metal," *J. Am. Chem. Soc. 115*:891–901 (1993).

Trost, B.M., and Lautens, M., "Chemoselectivity and Stereocontrol in Molybdenum–Catalyzed Allylic Alkylations," *J. Am. Chem. Soc. 109*:1469–1478 (1987).

Trost, B.M., and Lautens, M., "Regiochemical Diversity in Allylic Alkylations via Molybdenum Catalysts," *Tetrahedron 43*:21 (4817–4840 (1987).

Trost, B.M., and Merlic, C.A., "Ligand Dependence of Molybdenum–Catalyzed Alkylations. Molybdenum–Isonitrile Complexes as a New Class of Highly Reactive Alkylation Catalysts," *J. Am. Chem. Soc. 112*:9590–9600 (1990).

Trost, B.M., and Van Vranken, D.L., "Asymmetric Ligands for Transition–Metal–Catalyzed Reactions: 2–Diphenylphosphinobenzoyl Derivatives of $C_2$–Symmetric Diols and Diamines," *Angew. Chem. Int. Ed. Engl. 31*(2):228–230 (1992).

Trost, B.M., et al., "A Modular Approach for Ligand Design for Asymmetric Allylic Alkylations via Enantioselective Palladium–Catalyzed Ionizations," *J. Am. Chem. Soc. 114*:9327–9343 (1992).

*Primary Examiner*—Alan L. Rotman
*Assistant Examiner*—Rita Desai
*Attorney, Agent, or Firm*—LeeAnn Gorthey; Dehlinger and Associates

[57] ABSTRACT

Complexes of a selected class of chiral ligands with molybdenum, tungsten or chromium, preferably molybdenum, are effective as catalysts in highly enantioselective and regioselective alkylation of allylic substrates. Such compositions provide a versatile and low-cost alternative to existing catalysts.

8 Claims, 4 Drawing Sheets

CATALYTIC COMPOSITIONS AND METHODS FOR ASYMMETRIC ALLYLIC ALKYLATION

This application claims the priority of U.S. Provisional Application No. 60/068,128 filed Dec. 19, 1997, which is incorporated herein by reference in its entirety.

This invention was made with government support under contract 5R37 GM13598-30 awarded by the National Institutes of Health. Accordingly, the United States Government has certain rights in this invention.

FIELD OF THE INVENTION

The present invention relates to catalytic methods and compositions for use in highly regioselective and enantioselective alkylations of allylic substrates. Molybdenum, tungsten and chromium complexes of chiral ligands having such catalytic activity, particularly the molybdenum complexes, are described, along with methods for their use.

REFERENCES

Adolfsson, H. and Moberg, C., *Tetrahedron: Asymmetry* 6:2023 (1995).
Boudreau, C. et al., U.S. Pat. No. 5,574,186 (1996).
Collman, J. P. et al., *Science* 26:1404 (1993).
Dvorak, D. et al., *J. Am. Chem. Soc.* 117:6130 (1995) and references cited therein.
Fenton, R. R. et al., *J. Coord. Chem.* 23:291 (1991).
Godleski, S. A., in "Comprehensive Organic Synthesis," Trost, B. M., Fleming, I., and Semmelhack, M. F., eds.; Permagon Press, Oxford, 1991, Vol. 4, pp 585–662.
Hammen, P. D. et al., *Synth. Commun.* 21:2157 (1991).
Jacobsen, E. N. et al., *J. Am. Chem. Soc.* 112:2801 (1990); also U.S. Pat. No. 5,663,393 (1997).
Jacobsen, E. N. et al. U.S. Pat. No. 5,665,890 (1997).
Katsuki, T. *Tetrahedron Lett.* 31:7345 (1990).
Katsuki, T. and Sharpless, K. B., U.S. Pat. No. 4,471,130 (1984).
Lloyd-Jones, G. C. and Pfalz, A. *Angew. Chem. Int. Ed. Engl.* 34:462 (1995).
Merlic, C. A., Ph.D. Thesis, University of Wisconsin, 1988
Prétot, R. and Pfalz, A., *Angew. Chem. Int. Ed. Engl.* 37:323 (1998).
Rubio, A. and Liebeskind, L. S., *J. Am. Chem. Soc.* 115: 891 (1993).
Saigo, K. et al., *Bull. Chem. Soc. Japan* 59(3):931 (1986).
Singaram, B. et al., U.S. Pat. No. 5,367,073 (1994).
Trost, B. M. et al., *J. Am. Chem. Soc.* 109:2176 (1987).
Trost, B. M. and Hachiya, I., *J. Am. Chem. Soc.* 120:1104 (1998).
Trost, B. M. and Hung, M.-H., *J. Am. Chem. Soc.* 105: 7757 (1983).
Trost, B. M. and Lautens, M., *J. Am. Chem. Soc.* 104: 5543 (1982).
Trost, B. M. and Lautens, M., *J. Am. Chem. Soc.* 109: 1469 (1987).
Trost, B. M. and Lautens, M., *Tetrahedron* 43: 4817 (1987), and references cited therein.
Trost, B. M. and Merlic, C. A., *J. Am. Chem. Soc.* 112: 9590 (1990).
Trost, B. M. and Van Vranken, D. L., *Angew. Chem. Int. Ed. Engl.* 31:228 (1992).

BACKGROUND OF THE INVENTION

Interest in molybdenum- and tungsten -catalyzed reactions of allyl substrates with nucleophiles has been promoted by the regioselectivity shown by these complexes, as compared to that of palladium complexes. See, for example, for molybdenum, Trost and Merlic, 1990, Rubio and Liebeskind, 1993, Trost and Hachiya, 1998; and for tungsten, Trost and Hung, 1983, and Trost et al., 1987. Palladium catalyzed reactions generally provide products from attack at the less substituted terminus. This regiochemistry (shown at eq 1, path a in FIG. 1) is particularly favored for alkylation of aryl-substituted allyl systems, even with catalysts having chiral ligands (Godleski, 1991). Molybdenum and tungsten catalysts, on the other hand, generally favor attack at the more substituted terminus (eq 1, path b). Complexes of these metals are also less costly than palladium catalysts.

Such alkylations have shown limitations, however. For example, molybdenum-catalyzed alkylations of cinnamyl substrates, using dimethyl malonate, have been shown to favor attack at the less substituted allyl terminus (Trost and Lautens, 1982, 1987; Trost and Merlic, 1990). In general, there have been no reports, prior to the studies described herein, of molybdenum-catalyzed alkylations showing both high regio- and enantioselectivity. Early studies utilizing a variety of chiral nitrogen based ligands for molybdenum failed to give any appreciable asymmetric induction (Merlic, 1988). A study utilizing tungsten catalysts with chiral phosphino-oxazoline ligands reported that the isostructural molybdenum complex was "not useful as a catalyst" (Lloyd-Jones & Pflatz, 1995).

Products of the type shown in reaction path (b), having high optical purity, would find great value as building blocks in the synthesis of biologically useful compounds. A low-cost, versatile, stereoselective catalytic route to such compounds would thus be desirable.

SUMMARY OF THE INVENTION

In one aspect, the invention provides a catalytic organometallic composition which is effective to catalyze the enantioselective alkylation of an allyl group bearing a leaving group at its allylic position. The composition comprises a central metal atom, selected from the group consisting of molybdenum, tungsten, and chromium, and coordinated thereto, a chiral ligand $L^1$, and preferably a single such ligand $L^1$. The metal atom is preferably molybdenum or tungsten, and more preferably molybdenum.

The ligand $L^1$ comprises (i) a chiral component, derived from a chiral diamine, diol, or amino alcohol. This component has first and second chiral centers, each substituted with a group X selected from —O— or —NR—, where R is hydrogen or lower alkyl. Linked to each said group X is (ii) a binding group $Cy_N$, which comprises a heterocyclic group having a ring nitrogen atom effective to bind to said central metal atom. The heterocyclic group is optionally substituted with one or more groups selected from alkyl, alkenyl, aryl, aralkyl, alkoxy, aryloxy, acyl, acyloxy, amide, tertiary amine, nitro, or halogen, and may be fused to one or more additional rings.

In preferred embodiments, the first and second chiral centers of the chiral components are substituted with groups $R^1$ and $R^2$, respectively. In one embodiment, $R^1$ and $R^2$ are independently selected from aryl, heteroaryl, aralkyl, carbocycle, or heterocycle, and are optionally substituted with one or more groups selected from alkyl, alkenyl, aryl, aralkyl, alkoxy, aryloxy, acyl, acyloxy, amide, tertiary amine, nitro, or halogen. In one preferred embodiment, $R^1=R^2=$phenyl.

Alternatively, $R^1$ and $R^2$ together form a carbocyclic or heterocyclic ring, which is optionally substituted with one or more groups selected from alkyl, alkenyl, aryl, aralkyl, alkoxy, aryloxy, acyl, acyloxy, amide, tertiary amine, nitro, or halogen, and which may be fused to one or more additional rings. A ring formed by $R^1$ and $R^2$ is preferably a 5- to 7-membered carbocyclic ring, or a 5- to 7-membered heterocyclic ring having 3 to 6 carbon ring atoms and the remaining ring atoms selected from oxygen and nitrogen.

The chiral centers of the chiral component may be connected by a direct bond or by a chain of one to three atoms comprising linkages selected from alkyl, alkyl ether, alkyl amino, or a combination thereof. In preferred embodiments, the chiral centers are connected by a direct bond, and the chiral component is thereby derived from a chiral 1,2-diol, -diamine, or -amino alcohol, and preferably a chiral 1,2-diamine. Preferred examples include 1R,2R-trans-diaminocyclohexane, 1S,2S-trans-diaminocyclohexane, 1R,2R-trans-diphenyl-1,2-ethanediamine, and 1S,2S-trans-diphenyl- 1,2-ethanediamine. Other suitable diamines include 1R,2R-trans-diaminocycloheptane, 5R,6R-trans-5,6-diaminoindan, 3R,4R-trans-3,4-diamino-N-benzylpyrrolidine, and their S,S-counterparts.

Each heterocyclic binding group $Cy_N$ of ligand $L^1$ is preferably a 5- to 7-membered ring having 1 to 6 carbon ring atoms, with the remaining ring atoms selected from oxygen and nitrogen. Heteroaryl groups, such as pyridine, pyrimidine, triazine, tetrazine, pyrazole, triazole, tetrazole, quinoline, and isoquinoline, are particularly preferred, with pyridine being most preferred.

The group $Cy_N$ is linked, preferably at a ring carbon atom adjacent said ring nitrogen atom, to a group X of the chiral component, via a carbonyl or sulfonyl linkage, preferably a carbonyl linkage. A 2-pyridyl group, linked to the group X via a carbonyl linkage, is a particularly preferred binding group. N,N'-1R,2R-cyclohexanediylbis(2-pyridine carboxamide)), represented herein as ligand I, and its S,S-counterpart, are particularly preferred ligands. Other suitable ligands include those represented herein as ligands II–VIII and their mirror image counterparts.

The catalytic organometallic composition of the invention is the product of a process which comprises contacting, in a suitable solvent, a chiral ligand $L^1$, as defined above, with a hexacoordinate complex (also referred to herein as the starting complex or precomplex) of a metal selected from tungsten (0), chromium (0), and molybdenum(0). Preferred embodiments of the ligand $L^1$ are also as defined above. Tungsten and molybdenum complexes are preferred, with molybdenum being particularly preferred. Upon such contacting, the complex undergoes a ligand exchange reaction, such that $L^1$ becomes coordinated to the metal atom. The resulting composition is effective to catalyze the enantioselective alkylation of an allyl group bearing a leaving group at its allylic position.

In the above process, the molar ratio of the ligand $L^1$ added to the hexacoordinate precomplex is between about 2:1 and about 1:1, and preferably between about 1.1:1 and about 1.5:1. The hexacoordinate precomplex comprises ligands which form a stable complex with the metal and are displacable by ligand $L^1$ under the conditions of the ligand exchange. Such ligands include CO, cycloheptatriene, lower alkyl nitrile, and lower alkyl isonitrile. Preferred precomplexes for the preparation of the molybdenum catalysts include $Mo(h^3-C_7H_8)(CO)_3$ (cycloheptatriene molybdenum tricarbonyl), $Mo(CO)_3(CH_3CH_2CN)_3$, and $Mo(CO)_6$.

In another aspect, the invention provides a method of selectively alkylating an allyl group bearing a leaving group at the allylic position, under conditions effective to produce an alkylated product which is enriched in one of the possible isomeric products of such alkylation. The alkylation method comprises reacting the allyl group with an alkylating agent, in the presence of a catalytic amount of an alkylating catalyst. The alkylating catalyst is an octahedral organometallic complex having a central metal atom selected from the group consisting of molybdenum, tungsten, and chromium, and coordinated thereto, a chiral ligand $L^1$, as defined above. Preferred embodiments of the ligand $L^1$ are also defined above. The central metal atom is preferably molybdenum or tungsten, and more preferably molybdenum.

In a related aspect, the method comprises reacting such a substrate with an alkylating agent in the presence of a catalytic composition formed by contacting, in a suitable solvent, catalytic amounts of (i) a hexacoordinate complex of a metal selected from the group consisting of molybdenum (0), tungsten (0), and chromium (0) and (ii) a chiral ligand $L^1$, as defined above. Preferred embodiments of the ligand $L^1$ and the hexacoordinate complex are as defined above.

The mole percent of said catalyst with respect to said substrate is preferably between about 0.5% and about 15%, and more preferably between about 1% and about 10%.

The reaction is carried out under conditions effective to produce an alkylated product which is enriched in one of the possible isomeric products of such alkylation. In one aspect, the alkylation is enantioselective, and preferably produces an alkylated product having an enantiomeric excess greater than 75%, preferably greater than 85% and more preferably greater than 95%. In another aspect, when the allyl group is nonsymmetrically substituted at its termini, the alkylation is regioselective, such that said allyl group is alkylated at its more sterically hindered terminus. Preferably, the regioselectivity of alkylation, defined as the ratio of product alkylated at the more sterically hindered terminus to product alkylated at the less sterically hindered terminus, is greater than 3:1, and more preferably greater than 9:1.

Preferred allyl substrates for the reaction are those in which the allyl group is substituted at one terminus with a substituent selected from aryl, heteroaryl, alkenyl, alkynyl, and alkyl. The reaction is especially advantageous for substrates in which neither allyl terminus is aryl substituted. This includes those in which one terminus is substituted with an alkyl group or with a non-aromatic conjugated polyene or enyne. In another embodiment of the method, where the allyl group has identical non-hydrogen substituents at its termini (with the exception of the leaving group), the alkylation is enantioselective with respect to the new chiral center formed at the alkylated terminus of said allyl group.

The alkylating agent is a preferably a stabilized carbanion, such as a carbanion of the form $EE'RC^-M^+$, where E and E' are electron-withdrawing substituents, and $M^+$ is a positively charged counterion. E and E', which may be the same or different, are preferably selected from the group consisting of keto, carboxylic ester, cyano, and sulfonyl, and most preferably keto and carboxylic ester.

In a preferred embodiment of the method, the catalyst is formed in situ by ligand exchange of a soluble hexacoordinate molybdenum(0) complex with ligand $L^1$. The complex comprises ligands which are effective to form a stable complex with Mo(0) and which are displacable by ligand $L^1$ under the conditions of the ligand exchange. Preferred ligands include cycloheptatriene, CO, lower alkyl nitrile, and lower alkyl isonitrile.

These and other objects and features of the invention will become more fully apparent when the following detailed description of the invention is read in conjunction with the accompanying drawings.

DETAILED DESCRIPTION OF THE INVENTION

I. Definitions

Figure 1:
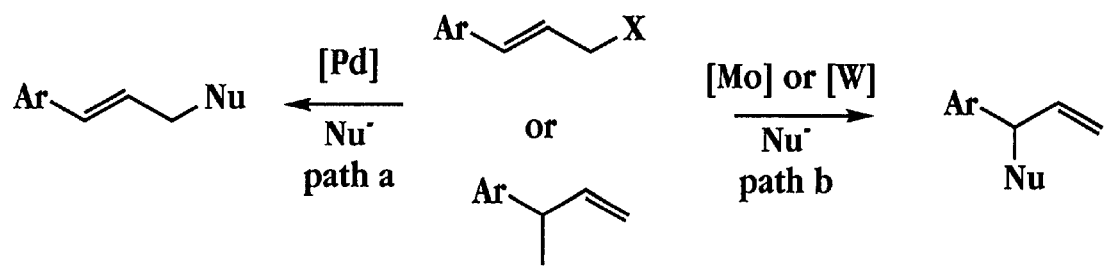
FIG. 1 shows the generally favored regioselectivity of allylic alkylation using palladium catalysts (a) and using molybdenum and tungsten catalysts (b)

The terms below have the following meanings unless indicated otherwise.

"Enantiomeric excess" or "e.e." refers to the quantity E1–E2, where E1 is the fraction of a compound having one enantiomeric configuration, and E2 is the fraction having the mirror image configuration.

"Asymmetric alkylation" or "enantioselective alkylation" refers to an alkylation reaction which produces one possible enantiomer of an alkylated center in a product in excess over the other enantiomer.

In an allyl group, that is, a three-carbon moiety having a double bond between carbons 1 and 2 and a single bond between carbons 2 and 3, the "allylic position" is the 3 position, and the "termini" are the 1 and 3 positions.

A "binding group", as used herein in reference to chiral ligands used in the catalysts of the invention, refers to a heterocylic group, defined herein as $Cy_N$, which contains a ring nitrogen which binds to the central metal atom in the catalyst.

A "chiral component", as used herein in reference to chiral ligands used in the catalysts of the invention, refers to a chiral diol, diamino, or amino alcohol moiety which forms a chiral scaffold to which two binding groups, as defined herein, are linked. The oxygen and/or nitrogen atoms of the diol, diamino or amino alcohol moiety may also participate in binding to the central metal atom in the catalyst.

"Alkyl" refers to a fully saturated monovalent radical containing carbon and hydrogen, and which may be cyclic, branched or a straight chain. Examples of alkyl groups are methyl, ethyl, n-butyl, n-heptyl, isopropyl, 2-methylpropyl, cyclopropyl, cyclopropylmethyl, cyclobutyl, cyclopentyl, cyclopentylethyl, and cyclohexyl.

"Lower alkyl" refers to an alkyl radical of one to six carbon atoms, as exemplified by methyl, ethyl, n-butyl, i-butyl, t-butyl, isoamyl, n-pentyl, and isopentyl.

"Acyl" and "acyloxy" refer to groups having the form —C(O)R or —OC(O)R, respectively, where R is an alkyl, aryl, or an aralkyl group.

"Aryl" refers to a substituted or unsubstituted monovalent aromatic radical having a single ring (e.g., phenyl) or two condensed rings (e.g., naphthyl). Other examples include heterocyclic aromatic ring groups having one or more nitrogen, oxygen, or sulfur atoms in the ring, such as furyl, pyrrole, pyridyl, and indole. "Aralkyl" refers to an alkyl, preferably lower alkyl, substituent which is further substituted with an aryl group.

II. Catalysts for Asymmetric Alkylation

The asymmetric catalysts of the invention are octahedral complexes of molybdenum, tungsten, or chromium with a particular class of chiral ligand. Complexes of molybdenum or tungsten are preferred, with molybdenum being most preferred. According to an important feature of the invention, such catalysts are effective to catalyze the alkylation of allylic substrates, giving a product which is enriched in one of the possible isomeric products of such alkylation. Specifically, use of the catalysts provides high enantioselectivity and high regioselectivity, as demonstrated below.

A. The Chiral Ligand

A1. Chiral Component

The chiral ligand, designated $L^1$, can be considered in terms of structural components, termed herein a chiral component and two binding components. A linearized structure of a representative ligand is given below:

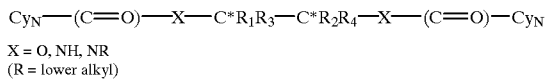

$X = O, NH, NR$
(R = lower alkyl)

The chiral component, represented by the central portion of the structure, is derived from a chiral diamine, diol, or amino alcohol. The amine and/or alcohol moieties are linked to first and second chiral centers, respectively (represented by starred carbons), in the molecule. In preferred embodiments, the chiral centers are connected by a direct bond, as shown, that is, the diamine, diol, or amino alcohol is a 1,2 system. However, chiral components having intervening bonds between the chiral centers, e.g. 1,3-, 1,4-, or 1,5-systems, can also be effective. In such cases, the chiral centers are connected by a chain of one to three atoms comprising linkages selected from alkyl (carbon-carbon) alkyl ether (carbon-oxygen), alkyl amino (carbon-nitrogen), or a combination thereof. Examples of compounds based on chiral diols and diamines of this type are shown, for example, in Trost & Van Vranken, 1992.

Each of chiral centers is further substituted with groups $R^1$ and $R^2$, respectively. These groups may be the same or different. The groups may be separate substituents, independently selected from aryl, heteroaryl, aralkyl, cycloalkyl, or heterocyclyl. Examples include, but are by no means limited to, phenyl, pyridyl, benzyl, naphthyl, cyclohexyl, furanyl, and pyranyl. Preferably, $R^1=R^2$.

$R^1$ and $R^2$ may also together form a carbocyclic or heterocyclic ring. Preferably, they form a 5- to 7-membered carbocyclic ring, or a 5- to 7-membered heterocyclic ring having 3 to 6 carbon ring atoms, with the remaining ring atoms selected from oxygen and nitrogen. Preferably, the heterocyclic ring contains one or two heteroatoms. Examples include, but are not limited to, piperidine, piperazine, pyrrolidine, morpholine, di- or tetrahydrofuran, and di- or tetrahydropyran. In all cases, $R^1$ and $R^2$, or the ring formed thereby, may be unsubstituted, or it may be substituted with one or more groups selected from alkyl, alkenyl, aryl, aralkyl, alkoxy, aryloxy, acyl, acyloxy, amide, tertiary amine, nitro, or halogen. Substituents to be avoided are those with active (acidic) hydrogens, such as phenolic groups or primary or secondary amines. $R^1$ and $R^2$, or the ring formed thereby, may also be fused to one or more additional rings.

As shown in the structure above, the chiral centers also have substituents $R^3$ and $R^4$ to provide tetravalent carbon. Although $R^3$ and $R^4$ are typically hydrogen, chiral components with tetrasubstituted chiral centers may also be used, providing, of course, that neither center has two identical substituents.

A distinctive type of chiral ligand, also suitable for use in the present catalysts, is that in which $R^1$ and $R^2$ are naphthyl groups which are linked to form a 1,1'-binaphthyl system (or analogous multinuclear systems). In such cases, for use in the present catalysts, the amine and/or alcohol groups of the chiral component are at the 2 and 2'-positions. Although these positions are not chiral centers in the conventional sense (i.e. they do not have four different substituents), the naphthyl groups form a helical system possessing what is termed axial chirality.

Figure 2A:
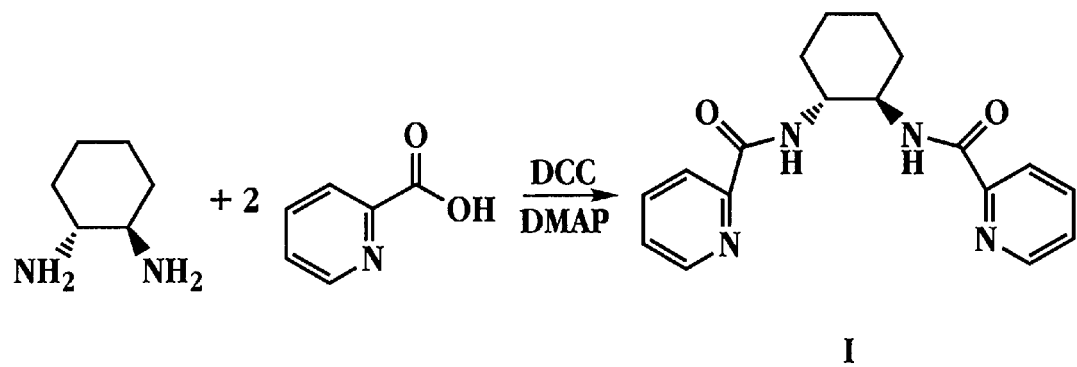
FIGS. 2A–2D show the preparation of several representative chiral ligands which may be employed in the chiral molybdenum catalyst of the invention.
Figure 2B:
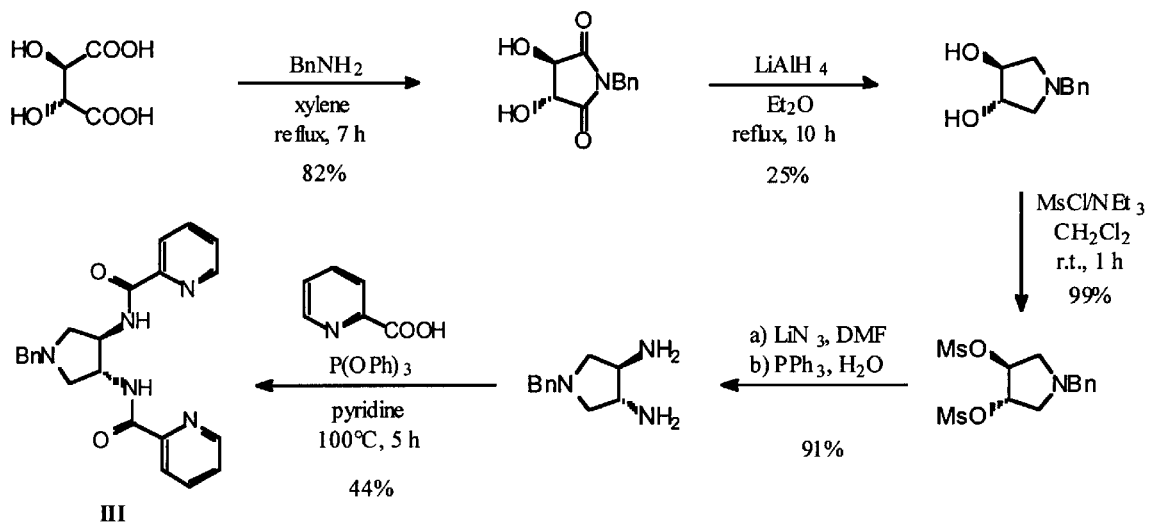

Preferred chiral components are derived from chiral 1,2-diamines. Of this group, those is which $R^1$ and $R^2$ form a ring are preferred. A particularly preferred chiral diamine of this class is 1R,2R-trans-diaminocyclohexane (see FIG. 2A) or its enantiomer, 1S,2S-trans-diaminocyclohexane, both of which are commercially available. FIGS. 2–3 show additional chiral ligands based on 5- and 7-membered rings. Also preferred are diamines having bulky substituents, such as trans-1,2-diamino-1,2-diphenylethane. Preparation of several representative chiral ligands is described below.

Many such chiral diamines, diols, and amino alcohols are commercially available. Such compounds can also be prepared from naturally occurring chiral precursors, e.g. amino acids, saccharides, tartrates, etc., using established synthetic procedures. Chiral compounds may also be prepared from achiral or racemic precursors using known synthetic methods having high stereoselectivity. The development of such methods has been an active field of research for many years and is the subject of many articles, books and treatises. Well known examples which are particularly useful for preparation of the present ligands include the asymmetric epoxidation of allylic alcohols (Katsuki and Sharpless) and other olefins (e.g. Jacobsen 1990; Collman, 1993). The epoxides can easily be converted to chiral 1,2-diols or amino alcohols by ring opening with an appropriate nucleophile, e.g., azide followed by hydrogenation to give the amino alcohol. Hydroboration of enamines has been used to produce chiral β-amino alcohols (Singaram, 1994). Other reactions that could be useful in preparing the present ligands include the stereoselective reduction of keto oximes (Boudreau, 1996) and bis-imines (Neumann, 1992) and the enantioselective ring opening of epoxides and other labile rings (Jacobsen, 1997).

In many cases, particularly for compounds which can form crystalline salts, e.g. many amines, optical resolution can provide compounds of high optical purity. For example, optical resolution of racemic 1,2-diphenylethanediamine gave the (+) and (−) enantiomers in over 99% and 97% optical purity, respectively (Saigo et al., 1986), and racemic trans-1,2-diaminocyclohexane was resolved to >99% optical purity via the lactic acid salt (Imaoka, 1995). Chromatography of racemic compounds on chiral supports has also been found useful.

A2. Binding Components

Linked to the chiral amine and/or alcohol moieties in the chiral diol, diamine, or amino alcohol are two groups referred to herein as binding groups, represented and shown in the linearized structure above as $Cy_N$ and $Cy_{N'}$. The binding groups, which are preferably the same but may be different, are heterocyclic rings, each having a ring nitrogen atom effective to bind to the central metal atom in the catalytic complex. Each heterocyclic group is preferably a 5- to 7-membered ring having 1 to 6 carbon atoms, with the remaining ring atoms selected from oxygen and nitrogen. Examples of such heterocycles include pyridine, pyrimidine, pyrazine, triazine, triazole, pyrazole, pyrrole, isopyrrole, pyrrolidine, imidazole, oxazole, imidazole, isoxazole, and the like, and multiring structures such as benzoxazole, benzimidazole, indole, quinoline and isoquinoline. Preferred classes include carbon-nitrogen aromatic rings. Among these groups, mononuclear 6-membered rings, e.g. pyridine and pyrimidine, are preferred, and pyridine is particularly preferred. Each binding group $Cy_N$ may be substituted with one or more groups selected from alkyl, alkenyl, aryl, aralkyl, alkoxy, aryloxy, acyl, acyloxy, amide, tertiary amine, nitro, or halogen, and may be fused to one or more additional rings.

The binding group is linked to the chiral component, or more specifically, to the amine and/or alcohol moieties of the chiral component, with such linkage preferably at a ring carbon adjacent to the binding ring nitrogen. Accordingly, a 2-pyridyl group is a preferred binding group. The group is preferably linked to the chiral component via a carbonyl linkage, e.g. an ester or amide, as shown in structures I–VIII (FIGS. 2 and 3). Such linkages are readily prepared from precursors of the chiral and binding components of the ligand, as described below. However, other stable linkages which result in a similar ligand geometry may also be used.

B. Preparation of the Chiral Ligand

Chiral ligands as described above are conveniently prepared by condensation reaction of the chiral component, that is, a chiral diamine, diol, or amino alcohol, with a suitable carboxylic acid derivative, or, alternatively, a sulfonic acid derivative, of the component or components represented by $Cy_N$. A typical preparation is shown in FIG. 2A. DCC (dicyclohexylcarbodiimide)-mediated coupling of (1R,2R)-trans-diaminocyclohexane with 2-pyridine carboxylic acid (picolinic acid), or with a more reactive acid derivative such as an ester, anhydride or acid halide, catalyzed by DMAP (dimethylaminopyridine), provides the chiral ligand I(N,N'-1R,2R-cyclohexanediylbis(2-pyridinecarboxamide). Ligands IV and V, based on cycloheptane and indan, respectively (see FIG. 3), may be prepared in a similar manner. Chiral ligand II ((1R,2R-N-N-bis(2-pyridine carboxamide)-1,2-diamino-1,2-diphenyl ethane; FIG. 3) may be prepared according to the method of Fenton et al or Adolfsson et al. Pyrrolidine-based ligand III is readily available in six steps starting from natural (+)-tartaric acid, as shown in FIG. 2B. Condensation with benzylamine, followed by reduction with lithium aluminium hydride and mesylation, yielded the bismesylate. Conversion to the corresponding diazide and subsequent reduction afforded the diamine, which was converted in 44% yield to the pyrrolidine ligand III by coupling with picolinic acid in the presence of triphenylphosphite.

Figure 2C:
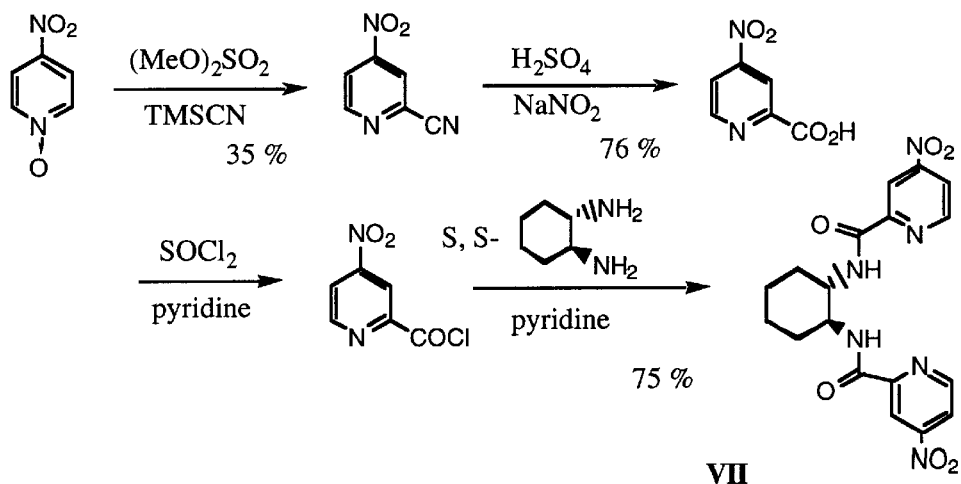
Figure 2D:
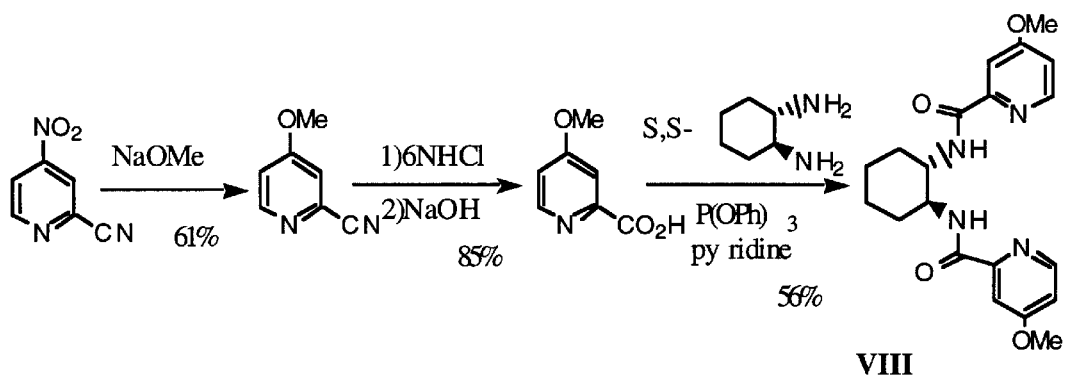
Figure 3:
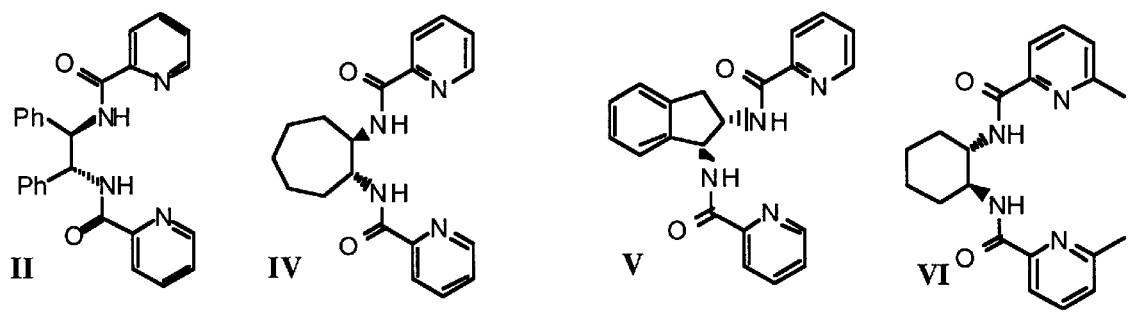
FIG. 3 shows additional examples of chiral ligands.

Ligand VII was synthesized as shown in FIG. 2C. Transformation of 4-nitro-2-cyano pyridine to 4-nitro-2-picolinic acid is followed by coupling of the corresponding acid chloride with 1S,2S-1,2-cyclohexanediamine. For synthesis of ligand VIII, 4-methoxy-2-picolinic acid was synthesized from 4-nitro-2-cyanopyridine, as shown in FIG. 2D, according to known methods, and coupled with 1S,2S-1,2-cyclohexanediamine. Ligand VI, shown in FIG. 3, is similarly prepared using 6-methyl 2-picolinic acid.

In preparing non-symmetrical ligands (where $Cy_N$ and $Cy_{N'}$ are different), one equivalent of the first carboxylic or sulfonic acid derivative is added, followed by one equivalent of the second carboxylic or sulfonic acid derivative. Typically, there is little interference from formation of symmetric, disubstituted ligand during the first reaction. A ligand having one pyridine and one quinoline binding group, for example, was prepared in this manner.

C. Preparation of Catalysts

The chiral catalyst is readily generated by ligand exchange of the ligand $L^1$ with a soluble octahedral complex of Mo(0), W(0), or Cr(0), where the molybdenum and tungsten complexes are preferred, and molybdenum particularly preferred. Suitable starting complexes are those having ligands which stabilize the starting complex, but are dispacable by the chiral ligand $L^1$ under mild conditions. Such ligands include, for example, cycloheptatriene, carbon monoxide, lower alkyl nitriles or isonitriles, or combinations thereof. Particularly preferred starting complexes are cycloheptatriene molybdenum tricarbonyl (Mo(h3-C7H8)(CO)$_3$), molybdenum hexacarbonyl (Mo(CO)$_6$) and molybdenum tris(propionitrile) triscarbonyl (CH$_3$CH$_2$CN)$_3$Mo(CO)$_3$.

The ligand $L^1$ and starting complex are stirred in an inert, nonprotic solvent such as THF or toluene, preferably in a molar ratio of about 1:1 to about 1:2, more preferably in the range of about 1:1.1 to about 1:1.5. In general, a larger scale preparation will call for a smaller excess of ligand $L^1$ over starting metal complex.

Although the exact structure of the active catalytic complex has not been definitively established, and is not intended to limit the invention, it is believed that the active complex has a ligand:metal ratio of 1:1 and is coordinatively unsaturated.

For the experiments described below, a 1:1.5 ratio of (CH$_3$CH$_2$CN)$_3$Mo(CO)$_3$ to ligand $L^1$ was used in preparing the catalyst, and the reaction was carried out at room temperature or in refluxing THF (about 65° C.). The catalytic complexes may be thus generated and then used in situ for alkylation, as described in the Examples below.

III. Asymmetric Allylic Alkylation Method

A. General Procedure

The asymmetric alkylation of the invention is carried out by contacting an allylic substrate and an alkylating agent with a solution containing a catalytic amount of a chiral catalyst as described above. In a preferred embodiment, the catalyst is generated in situ by reaction of a chiral ligand $L^1$ with a soluble starting complex, as described above. Generation of the catalyst is then followed by addition of the alkylating agent and the allylic substrate. In other embodiments of the method, the catalyst may be added to the substrate and alkylating agent.

All of these operations are carried out in a suitable aprotic and non-complexing solvent, such as, for example, THF, ether, toluene, other hydrocarbon solvents, chlorinated solvents, or a mixture thereof, in an inert atmosphere, e.g. dry nitrogen or argon. The reaction proceeds well both at room temperature and in refluxing THF (65° C.), with greater selectivities and longer reaction times typically resulting at lower temperatures, as shown, for example, in Table 1. A mixture of THF and toluene also gave excellent results. Optimum reaction time and temperature will vary based on factors such as the structure of the substrate, the level of catalyst, and the degree of selectivity desired, and can be determined by one of skill in the art using routine experimentation.

The catalyst is generally effective at levels of about 15 mole percent or less, with respect to the target allyl group. Preferred levels are in the range of about 0.5 to 15 mole percent, and more preferably 1 to 10 mole percent. Larger amounts of catalyst may be used for less reactive ligands and/or substrates.

The alkylating agent is a nucleophilic carbon species, preferably a stabilized carbanion derived from a malonate or beta-keto ester. Alkylating agents containing alkyl and allylic substitution at the attacking carbon were found to be effective (Table 1, lines 8–14). Reaction with other nucleophilic species, such as oxygen- or nitrogen-based nucleophiles, is also contemplated.

The substrate is a compound containing an allyl group which bears a leaving group at the allylic position. Alkylation of such a substrate according to the present method, using the catalytic complex described herein, is effective to produce an alkylated product which is enriched in one of the possible isomeric products of such alkylation. The benefits of the invention are most clearly seen with non-symmetrically substituted allyl groups. By "non-symmetrically substituted" is meant that the allyl group contains different groups (not considering the leaving group) at its termini, that is, at the 1 and 3 positions, where the 3 position is the allylic position. In such cases, both high regioselectivity and enantioselectivity are demonstrated, as discussed below.

Preliminary results have also shown that the catalytic compositions and methods are useful for enantioselective alkylation of symmetrically substituted allyl groups, that is, where the 1 and 3 positions have identical substituents, with the exception of the leaving group. A simple example of such a substrate is cyclopentene having a leaving group at the 3 position.

Figure 4:
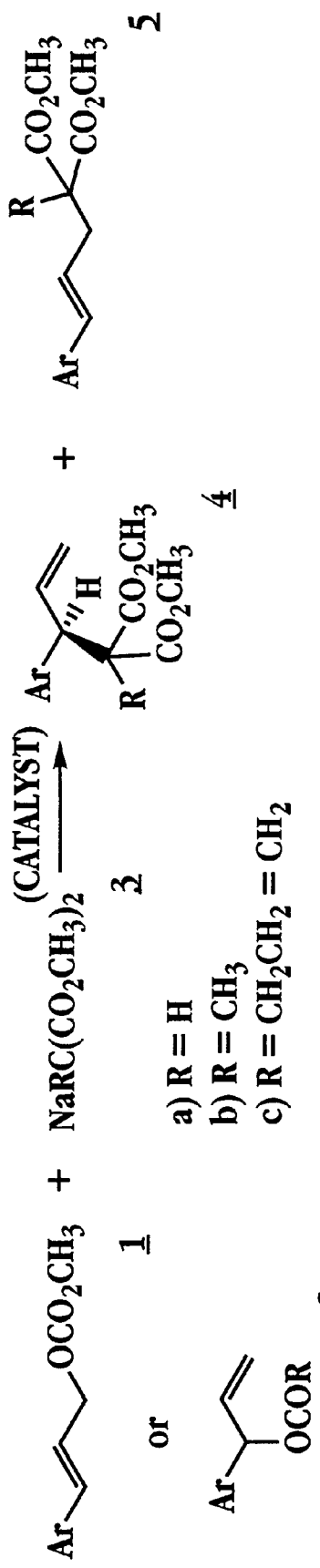
FIG. 4 shows the reaction of an allylic substrate with an alkylating agent, and the two possible products, formed by alkylation at the different termini of the allyl group.

FIG. 4 shows representative non-symmetrically substituted substrates 1 and 2, where the leaving group is a carbonate or acetate. These can be represented more generally by structures R'—CH=CH—CR"H—X (1) or R'—CHX—CH=CR"H (2), where X is a leaving group, and R' and R" are substituents, such as, for example, alkyl, alkenyl, aryl, alkynyl, or heteroaryl. Preferred substrates are those in which the more highly substituted terminus is remote from the leaving group, i.e. 1 as opposed to 2, although good results are also obtained with the latter type of substrate, as shown, for example, in Table I. Especially favorable substrates are those of structure 1 in which R' is aryl, heteroaryl, or alkenyl, that is, in which R' forms a conjugated system with the allylic double bond. R" is preferably hydrogen, although it may be a substituent. It was found, however, that introduction of an alkyl substituent on the higher substituted position of the allylic system (i.e. on the carbon bearing R') resulted in a decrease of the yield and a reversal, as well as a general reduction, in regioselectivity.

A very useful feature of the alkylation catalyst and method is the high regioselectivity favoring the more highly substituted terminus of the allyl group, as shown by the data presented herein. The reactions outlined in Table 1, for example, consistently gave a selectivity of about 83% (a 5:1 product ratio), and selectivities of about 97% (a 32:1 ratio), or greater, were common.

One general procedure for the reaction, using THF as solvent, is described in Example 1 below. This process was used, with variations in reaction time and temperature, in the alkylation of various substrates with a series of diethyl malonates, using chiral ligand I, to give the results shown in Table 1. In a typical reaction (entry 1), approximately 10 mol % of chiral molybdenum catalyst (based on the starting Mo complex) incorporating chiral ligand I was used in the alkylation of 1 (FIG. 4) with dimethyl sodiomalonate (3, R=H). An 88% yield of a 97:3 ratio of 4:5 (Ar=Ph, R=H) was obtained, with 4 having an e.e. of 99%. When the reaction was carried out at room temperature (entry 2) rather than at reflux, a good yield was still obtained, with somewhat improved regioselectivity and a similarly high e.e.

TABLE 1

Mo Catalyzed Asymmetric Allylic Alkylations[a]

| | 1 or 2 Ar | 3 R | T, °C. | Time, hrs | Yield[b], % | Ratio 4:5 | ee[c,d] 4 |
|---|---|---|---|---|---|---|---|
| 1 | 1, Ph | H | reflux | 3 | 88 | 32:1 | 99 |
| 2 | 1, Ph | H | r.t. | 3 | 70 (90) | 49:1 | 99 |
| 3 | 2a, Ph | H | reflux | 3 | 70 | 13:1 | 92 |
| 4 | 2a, Ph | H | r.t. | 3 | 61 (68) | 32:1 | 97 |
| 5 | 2a, 2-thienyl | H | reflux | 2 | 78 | 19:1 | 88 |
| 6 | 2a, 2-pyridyl | H | reflux | 2 | 69 (82) | 8:1 | 96 |
| 7 | 2a, 1-naphthyl | H | reflux | 2 | 82 | 99:1 | 87 |
| 8 | 1, Ph | CH₃ | reflux | 4 | 67 | 24:1 | 98[d] |
| 9 | 1, 2-furyl | CH₃ | reflux | 2 | 71 | 32:1 | 97 |
| 10 | 2b, 2-furyl | CH₃ | reflux | 2 | 65 | 32:1 | 87 |
| 11 | 2b, 2-furyl | CH₃ | r.t. | 18 | 54 | 99:1 | 95 |
| 12 | 2a, 2-pyridyl | CH₃ | reflux | 2 | 71 | 5:1 | 94 |
| 13 | 2a, 2-thienyl | CH₃ | reflux | 2 | 71 | 13:1 | 75 |
| 14 | 2b, 2-furyl | CH₂CH=CH₂ | r.t. | 12 | 50 | 99:1 | 98[e] |

[a]All reactions were performed with 10 mol % $(C_2H_5CN)_3Mo(CO)_3$, 15 mol % I in THF at 0.1 M.
[b]Isolated yields; yields in parentheses are based upon recovered starting material.
[c,d]Determined by chiral HPLC using Daicel Chiracel OD eluting with heptane-isopropanol. The major isomer was assigned as S by comparison to the literature for 4 (Ar = Ph, R = H) and 4 (Ar = 1-naphthyl, R = H), and the rest by analogy. Because of substituent priorities, however, the same absolute configuration of the product of reaction 8 (Ar = Ph) corresponds to the R configuration.
[e]The ee was determined on the subsequent transformation product.

Entries 5–7 show corresponding results obtained upon variation of the aromatic ring. An electron rich thiophene ring (entry 5), an electron deficient pyridine ring (entry 6), and a bulkier naphthalene substrate (entry 7) all gave good yields and selectivities.

Increasing the steric bulk of the nucleophile by using alkylating agent 3b (FIG. 4) gave similar excellent results with both carbocyclic and heterocyclic substrates (entries 8–12). Only in the case of the thiophene substrate was there some deterioration of the e.e. (75%) for the product (entry 13), although no attempt was made to optimize this reaction. The regioselectivity was still good (about 93%, or a 13:1 product ratio).

When the steric bulk of the alkylating agent was increased further, by using the allylmalonate nucleophile 3c, the regio- and enantio-selectivities were still excellent (entry 14). For the furan substrate bearing the leaving group at the secondary carbon, the acetate 2b, rather than the carbonate 2a, was employed.

The corresponding tungsten catalyst employing ligand I was also found to give high e.e.'s, but gave lower yields and required higher concentrations to give regioselectivities comparable to the molybdenum catalyst. When the reaction in entry 1 was conducted with the tungsten catalyst, generated by stirring a 1:1.5 mixture of $(C_2H_5CN)_3W(CO)_3$: ligand I in THF at 60° C., a modest yield of a 19:1 ratio of 4:5 (Ar=Ph, R=H), where 4 had an ee of 98%, was observed. Increasing the catalyst to 15 mol % increased the yield to 55% and the 4:5 ratio to 49:1, with 4 still having 98% ee.

The following sections serve to illustrate the scope of the reaction by showing the effect of varying different reaction parameters. It should be appreciated that the reaction is not limited to the embodiments and examples shown below.

B. Chiral Ligand

Table 2 shows the results of the Mo-catalyzed alkylation reaction of methyl cinnamyl carbonate using dimethylmalonate as the alkylating agent and catalysts prepared from ligands II and III (based on diphenylethane and pyrrolidine, respectively), shown in FIGS. 2 and 3. Both ligands gave good selectivity, as shown in Table, although turnover was generally lower than obtained with the cyclohexyl ligand I.

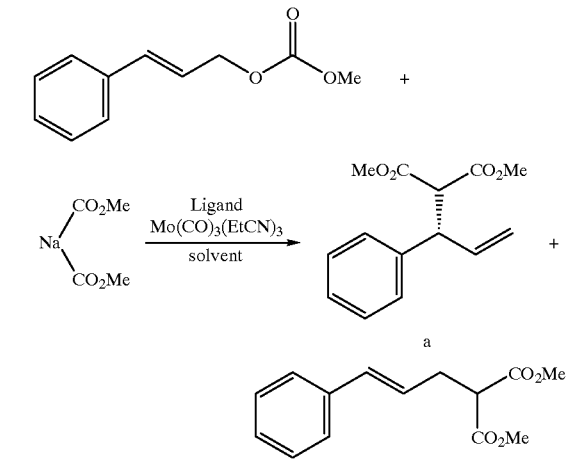

TABLE 2

Alkylation of Me cinnamyl carbonate with ligands II–III[a]

| Entry | ligand | solvent[b] | temp. [°C.] | time [h] | yield[b] (a + b) | ratio[c] (a:b) | ee[d] [%] |
|---|---|---|---|---|---|---|---|
| 1 | III | THF | 70 | 18 | 40 (55) | 82:18 | 94 |
| 2 | II | THF | 70 | 8 | 74 (89) | 92:8 | 98 |
| 3 | III | toluene/THF | 90 | 8 | 76 (98) | 89:11 | 94 |
| 4 | II | toluene/THF | 90 | 3 | 95 | 95:5 | 99 |
| 5[e] | II | toluene/THF | 90 | 20 | 46 | 70:30 | 86 |

[a]All reactions were performed in the presence of 0.1 eq $Mo(CO)_3(EtCN)_3$, 0.15 eq ligand, 1.0 eq carbonate, 2.2 eq dimethylmalonate and 2.0 eq NaH (≈0.1 molar).
[b]Isolated yields; yields in parentheses are based upon recovered starting material.

TABLE 2-continued

Alkylation of Me cinnamyl carbonate with ligands II–III[a]

| Entry | ligand | solvent[b] | temp. [° C.] | time [h] | yield[b] (a + b) | ratio[c] (a:b) | ee[d] [%] |
|---|---|---|---|---|---|---|---|

[c]Determined by 1H NMR spectroscopy.
[d]Determined by enantioselective HPLC. Assignment of the absolute stereochemistry of tne major enantiomer as S is based upon comparison of the optical rotation with literature values.
[e]Only 5 mol % (EtCN)$_3$Mo(CO)$_3$ was used.

The use of toluene/THF 1:1 as solvent was found to give excellent results. In the case of the pyrrolidine ligand III, the yield and regioselectivity improved and enantioselectivity was still high (entry 3). With the diphenyl ligand II, the reaction was complete after 3 hours, and the product was isolated in 95% yield with excellent regio- (95:5) and enantioselectivity (99% ee) (entry 4). In using this solvent system, the catalyst is prepared in toluene (60° C., 1 h), and the substrate and alkylating agent are added as a solution in THF (see Example 2).

Table 3 shows the reaction of several substrates with malonate using catalysts formed from ligands IV–VIII, shown in FIGS. 2 and 3. Thiophene and naphthalene derivatives were chosen as substrates since they were known to give less than optimum selectivity with the cyclohexyl ligand I.

A molybdenum catalyst prepared as described above and incorporating a non-symmetric ligand, having a 2-quinolinyl group in place of one of the pyridyl groups of ligand I, was found to give enantioselectivities similar to those obtained with ligand I, although reaction rates were generally slower.

C. Substrate

C1. Aromatic Polyenes

The alkylation of a variety of carbonate substrates using the diphenyl ligand II in toluene/THF 1:1 is shown in Table 4. All reactions were performed in the presence of 0.1 equiv Mo(CO)$_3$(EtCN)$_3$, 0.15 equiv ligand II, 2.2 equiv dimethylmalonate and 2.0 equiv sodium hydride in toluene/THF 1:1, according to the general procedure of Example 2.

The 2-furyl derivative 6 was alkylated in 71% yield with excellent regio- (95:5) and enantioselectivity (98%) (entry 1). Of this group, the best regioselectivity (98:2) was obtained with the 1-naphthyl carbonate 7, which was alkylated obtained in 91% yield, giving an enantiomeric excess of 87% (entry 2).

The diene system 8 (entry 3) also gave good results, proceeding in 3 hours to give excellent (95%) yield with good regioselectivity (12a/12b 86:14) and excellent enantioselectivity (98% ee). The $^1$H NMR spectra of the isolated product showed no traces of the product derived from alkylation at C5.

The aromatic triene substrate 9 (entry 4) was also converted with high enantioselectivity (97% ee), although the

TABLE 3

Use of Various Chiral Ligands

| Substrate | Ligand | Solvent | Temp, ° C. | Time, h | Yield, % | A/B | e.e. of A, % |
|---|---|---|---|---|---|---|---|
| R = Ph (upper structure) | IV | THF | 65 | 8 | 74 | 34/1 | 99 |
|  | V | THF | 65 | 18 | 63 (66) | 4.6/1 | 87 |
| R = 2-thiophenyl (lower structure) | IV | THF | 65 | 4.5 | 78 | 16/1 | 92 |
|  | IV | THF/toluene | 90 | 1.5 | 87 | 9.5/1 | 82 |
|  | VI | THF | 65 | 18 | 73 | 6.4/1 | 77 |
|  | VII | THF | RT | 47 | 29 (34) | 4.4/1 | 68 |
|  | VIII | THF | 65 | 3 | 83 | 12.7/1 | 84 |
| R = 1-naphthyl (lower structure) | IV | THF | 65 | 5 | 78 | 28.5/1 | 85 |
|  | VI | THF | 65 | 9 | 55 (72) | 12.5/1 | 79 |

Cycloheptyl ligand IV gave similar selectivity to that of the cyclohexyl ligand I, although reaction times were generally longer. Of the remaining ligands in this group, cyclohexyl ligand VII, having methoxy-substituted pyridyl binding groups, gave the best selectivity and the shortest reaction times.

turnover was somewhat lower. As in the case of substrate 8, this reaction proceeded with high regioselectivity, in the sense that no other alkylation products (i.e. derived from alkylation at C5 or C7), nor the corresponding cis isomer, were detected by $^1$H NMR. Furthermore, the linear product 13b was formed almost exclusively as the all-trans isomer.

TABLE 4

Asymmetric Mo-catalyzed alkylation with diphenyl ligand II substrate + Na-CH(CO₂Me)₂ → (Ligand II, (EtCN)₃Mo(CO)₃, THF/Toluene, 80–90°) → 10-13a (branched) + 10-13b (linear)

| entry | substrate | time [h] | R = | yield[a] (a + b) | ratio[b] (a:b) | ee[c] [%] |
|---|---|---|---|---|---|---|
| 1 | 6 (furan-CH=CH-CH₂-OC(O)OMe) | 10 | 2-furyl (10) | 71 (89) | 95:5 | 98 |
| 2 | 7 (1-naphthyl-CH(OC(O)OMe)-CH=CH₂) | 8 | 1-naphthyl (11) | 91 | 98:2 | 87 |
| 3 | 8 (Ph-CH=CH-CH=CH-CH₂-OC(O)OMe) | 3 | Ph-CH=CH- (12) | 95 | 86:14 | 98 |
| 4 | 9 (Ph-(CH=CH)₃-CH₂-OC(O)OMe) | 4 | Ph-(CH=CH)₂- (13) | 58 (92) | 84:16 | 97 |

[a] Isolated yields. Yields in parentheses are based upon recovered starting material.
[b] The ratio a:b was determined by ¹H NMR spectroscopy of the isolated products.
[c] Determined by enantioselective HPLC of the isolated products. The assignment of the absolute stereochemistry of the major enantiomer 10-13a is based upon comparison of the optical rotation with literature values for 11a.

C2. Non-Aromatic Substrates

Attempted alkylation of monoolefin substrates, such as, for example, methyl 2-butenyl carbonate, methyl (4-methyl-2-pentenyl) carbonate, and methyl (2-cyclopentenyl) carbonate, performed according to the general procedure of Example 2, either failed or generated only traces of alkylation product. However, reactions with conjugated polyenes and enynes were very successful, as described below. Reaction of several diene substrates is shown in Table 5.

TABLE 5

Asymmetric Mo-catalyzed alkylation of non-aromatic diene substrates.[a]

substrate 14-19 + Na-CH(CO2Me)2 →[Ligand I, Mo(CO)3(EtCN)3, THF/toluene 1:1, 80-90° C.] 20-25a + 20-25b

| entry | substrate | time [h] | R = | yield[b] (a + b) | ratio[c] (a:b) | ee[d] [%] |
|---|---|---|---|---|---|---|
| 1 | 14 (cyclohexenyl allyl methyl carbonate) | 3 | cyclohexenyl-CH(Me)- (20) | 91 | 92:8 | 94 |
| 2 | 15 | 3 | (21) | 89 (94) | 98:2 | 98 |
| 3[e] | 15 | 6 | (21) | 87 (95) | 94:6 | 97 |
| 4 | 16 | 3 | (23) | 81 (89) | 89:11 | ≈80[f] |
| 5 | 17 | 2 | (23) | 94 | 92:8 | 87 |
| 6 | 18 | 2 | (24) | 96 | 94:6 | 86 |

TABLE 5-continued

Asymmetric Mo-catalyzed alkylation of non-aromatic diene substrates.[a]

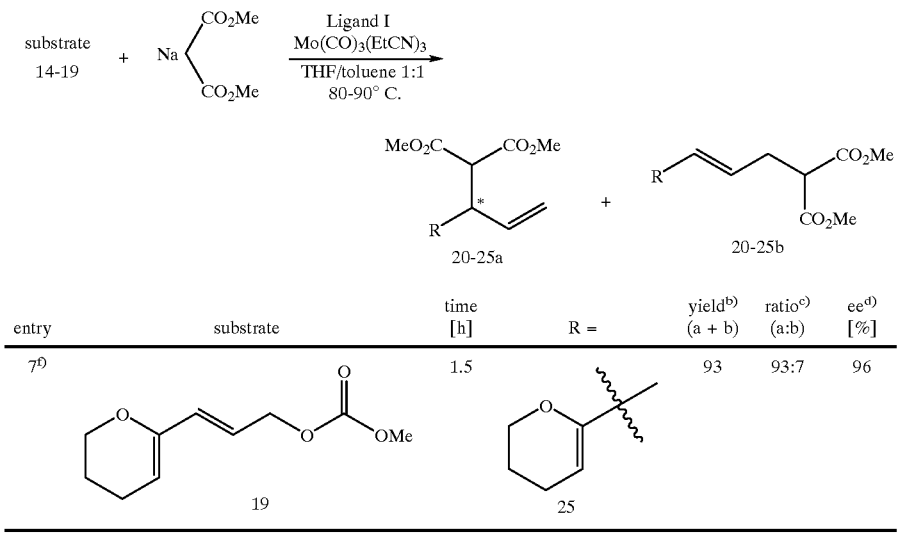

| entry | substrate | time [h] | R = | yield[b] (a + b) | ratio[c] (a:b) | ee[d] [%] |
|---|---|---|---|---|---|---|
| 7[f] | 19 | 1.5 | 25 | 93 | 93:7 | 96 |

[a] All reactions were performed in the presence of 0.1 equiv catalyst, 0.15 equiv ligand, 1.0 equiv substrate, 2.2 equiv dimethylmalonate and 2.0 equiv sodium hydride (≈0.1 molar).
[b] Isolated yields; yields in parentheses are based upon recovered starting material.
[c] Determined by 1H NMR spectroscopy of the isolated products.
[d] Determined with enantioselective HPLC from the isolated products.
[e] Ligand II was used.
[f] 20 mol % catalyst and 30 mol % ligand I were used.

Excellent results were obtained with the diene substrates 14 and 15, using either the cyclohexyl ligand I (entries 1–2) or the diphenyl ligand IV (entry 3). Substrates 16–18 (entries 4–6) were also alkylated in high yields and with good regioselectivities (>9:1), although the enantiomeric excesses were somewhat lower. Alkylation of the heterocyclic non-aromatic dihydropyran carbonate 19 was also successful (entry 7), although a larger amount of catalyst (20 mol %) was required for the reaction to proceed at an acceptable rate.

These results represent the first example to date of allylic alkylation of non-aromatic substrates, at the more highly substituted allylic position, in excellent yield and with very good regio- and enantioselectivity. Substrate 18, for example, was alkylated using the present method within 2 h in 96% yield, with very good regioselectivity (94:6) and with an enantiomeric excess of 86%. In comparison, using a recently described Pd catalyzed method (Prétot et al., 1998), the allylic regioisomer of the same carbonate 18 was alkylated in 75% yield, with much lower regio- and enantioselectivity (75:25 and 51% ee, respectively). (See also Section D, below, for discussion of alkyl substituted substrates).

Triene systems such as carbonates 26 or 27 were also alkylaed in good yields and excellent regio- and enantioselectivities (Table 6). In each case, only 10 mol % catalyst was needed and only one branched isomer (28a and 29a) was obtained. As in the case of the aromatic triene substrate 13, alkylation at C5 or C7 was not observed by $^1$H NMR spectroscopy.

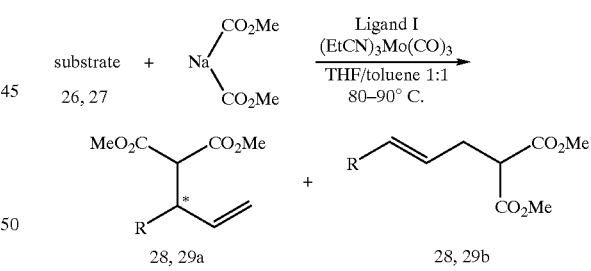

TABLE 6

Asymmetric Mo-catalyzed alkylation of non-aromatic triene substrates.

| entry | substrate | time [h] | R = | yield[a] (a + b) | ratio[b] (a:b) | ee[c] [%] |
|---|---|---|---|---|---|---|
| 1 | 26 | 2 | 28 | 70 (79) | 92:8 | 97 |
| 2 | 27 | 3 | 29 | 81 (85) | 91:9 | 98 |

[a] Isolated yields. Yields in parentheses are based upon recovered starting material.
[b] The ratio a:b was determined by 1H NMR spectroscopy of the isolated products.
[c] Absolute configurations were not determined.

The aromatic alkyne substrate 30, below, was alkylated with 10 mol % catalyst in high yield and with good regio- (84:16) and excellent enantioselectivity (99% ee). In contrast to these results, Pd-catalyzed reactions of such substrates were in many cases poorly stereoselective and produced cis/trans mixtures. For example, Pd(0)-catalyzed alkylation of carbonate 30 with malonate (5 mol % Pd$_2$(dba)$_3$·CHCl$_3$, 25 mol % PPh$_3$, THF, rt, 2 h) afforded a mixture of 31b and 31c in a ratio of 58:42.

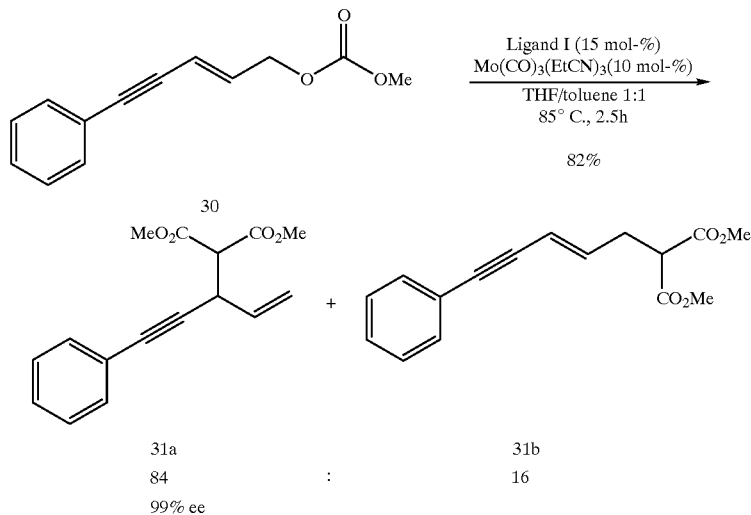

With the non-aromatic alkyne 32, the turnover was somewhat lower (Table 7, entry 1). Increasing the amount of catalyst to 20 mol %, however, gave a much better yield (81%) with good regio- (88:12) and excellent anantioselectivity (99% ee). With a phosphate leaving group, the alkylation product was obtained in good yield (82%) and enantioselectivity (96% ee) with less catalyst (10 mol %), although the regioselectivity was much lower (entry 4).

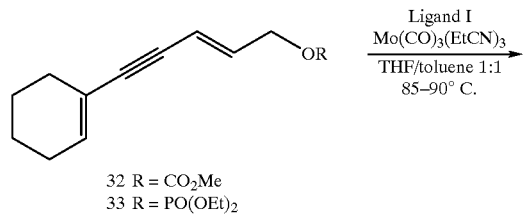

32 R = CO$_2$Me
33 R = PO(OEt)$_2$

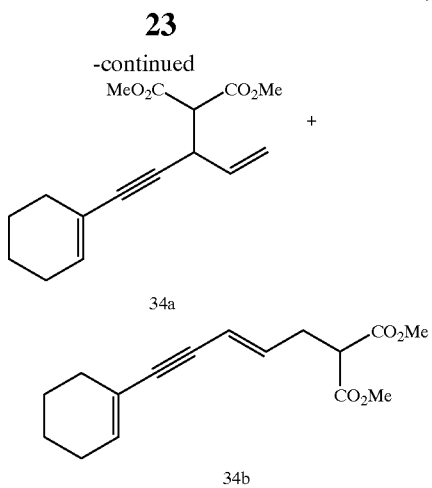

34a

34b

C3. Halogenated Substrates

The bromo-substituted aryl carbonate 35 was converted in 83% yield with good regio- (95:5) and enantioselectivity (90% ee) (Table 8).

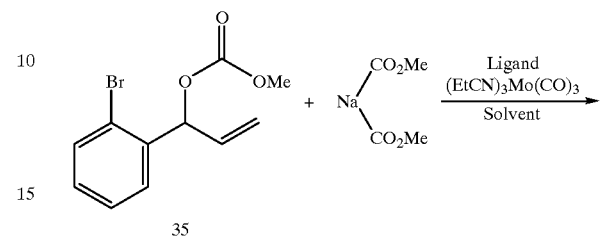

35

TABLE 7

Alkylation of non-aromatic alkyne substrates.

| entry | substrate | catalyst [mol-%] | additive | time [h] | yield[a] (34a + 34b) | ratio[b] (34a:34b) | ee[c] [%] |
|---|---|---|---|---|---|---|---|
| 1 | 32 | 10 | — | 3.5 | 36[d] | 79:21[e] | 97 |
| 2 | 32 | 20 | — | 4 | 81 (97) | 88:12 | 99 |
| 3 | 32 | 10 | DMSO[f] | 3.5 | 37% conversion[g] | 77:23[g] | ND[h] |
| 4 | 33 | 10 | — | 2 | 82 (95) | 66:34 | 96 |

[a] Isolated yields. Yields in parentheses are based upon recovered starting material. The two regioisomers were not separated.
[b] Determined by 1H NMR spectroscopy of the isolated products.
[c] Determined with enantioselective HPLC of the isolated products.
[d] Conversion was 47% according to 1H NMR spectroscopy of the crude mixture.
[e] The ratio the crude product was 77:23 (1H NMR).
[f] 10 mol % DMSO was added to the preformed catalyst (60° C. 1 h) before the substrate and malonate were added.
[g] According to 1H NMR spectroscopy of the crude mixture.
[h] Not determined.

It was also observed that formation of the minor linear product in the present reactions was stereoselective. The linear product was always obtained with very high trans selectivity, generally only traces of the cis isomer were detected. This stereoselectivity was observed not only for linear carbonates but for the branched substrates as well.

As described below under the discussion of leaving groups (Section D), the present reaction can also be successfully carried out on substituents having simple alkyl substitution at the allyl terminus (e.g. crotyl chloride).

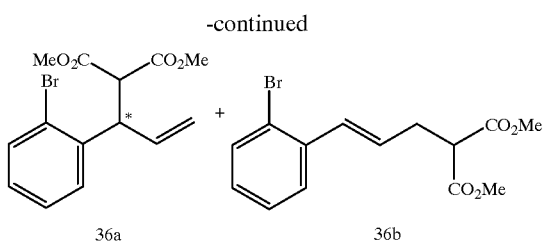

36a  36b

TABLE 8

Asymmetric Mo-catalyzed alkylation of the carbonate 35.[a]

| entry | ligand | solvent[b] | temp. [° C.] | time [h] | yield[c] (36a + 36b) | Ratio[d] (36a:36b) | ee[e] [%] |
|---|---|---|---|---|---|---|---|
| 1 | (±)-I | THF | 70 | 4 | 63 (94) | 94:6 | — |
| 2 | (S,S)-I | toluene/THF | 90 | 3 | 96 | 96:4 | 91 |
| 3 | III | toluene/THF | 90 | 14 | 85 | 91:9 | 88 |
| 4 | II | toluene/THF | 90 | 5 | 83 (95) | 95:5 | 90 |

[a] All reactions were performed in the presence of 0.1 eq Mo(CO)$_3$(EtCN)$_3$, 0.15 eq ligand, 1.0 eq substrate, 2.2 eq dimethylmalonate and 2.0 eq NaH.
[c] Isolated yields; yields in parentheses are based upon recovered starting material.
[d] Determined by 1H NMR spectroscopy.
[e] Determined by enantioselective HPLC.

As can be seen from Table 8, similar enantioselectivities were achieved with all ligands employed, although the regioselectivity was somewhat lower in the case of the pyrrolidine ligand III (entry 2–4). Again, use of toluene/THF as solvent gave higher turnover and better regioselectivity for ligand I (entries 1–2).

It should be appreciated that, although the structures of the present examples illustrate the utility and selectivity of the reaction, the allylic substrate may also form part of a more complex molecule, as in the synthesis of pharmaceutically useful chiral compounds.

D. Leaving Group

Preferred leaving groups are those which are displacable by a nucleophilic species under the conditions of the reaction, but which do not tend to dissociate without the participation of the nucleophile. These include, for example, the above described leaving groups (lower alkyl esters or carbonates) or chloride. Table 9 shows the effect on the reaction of variation of the leaving group.

TABLE 9

Variation of the leaving group[a]

| entry | substrate | solvent | temp. [° C.] | time [h] | yield[b] (a + b) | ratio[c] (a:b) | ee[d] [%] |
|---|---|---|---|---|---|---|---|
| 1 | 37 | THF | 70 | 3 | 88 | 97:3 | 99 |
| 2 | 37 | THF/toluene | 90 | 2 | 96 | 96:4 | 99 |
| 3 | 38 | THF/toluene | 90 | 12 | 75 (91) | 93:7 | 99 |
| 4 | 39 | THF/toluene | 90 | 4 | 94 | 93:7 | 99 |

[a]All reactions were performed in the presence of 0.1 equiv Mo(CO)$_3$(EtCN)$_3$, 0.15 equiv ligand, 1.0 equiv substrate, 2.2 equiv dimethylmalonate and 2.0 equiv sodium hydride.
[b]Isolated yields. Yields in parentheses are based upon recovered starting material.
[c]Determined by 1H NMR spectroscopy of the isolated product.
[d]Determined with enantioselective HPLC of the isolated product.

It has been shown that carbamate and trifluoroacetate are generally useful leaving groups for Mo-catalyzed alkylation reactions (Dvorak et al., 1995). As can be seen from Table 9, these groups, particularly trifluoroacetate, are also useful in the present reaction.

Variation of the leaving group was also investigated with the much less reactive crotyl substrate, using catalyst prepared from Mo(CO)$_3$(EtCN)$_3$ and ligand I. The results are shown in Table 10.

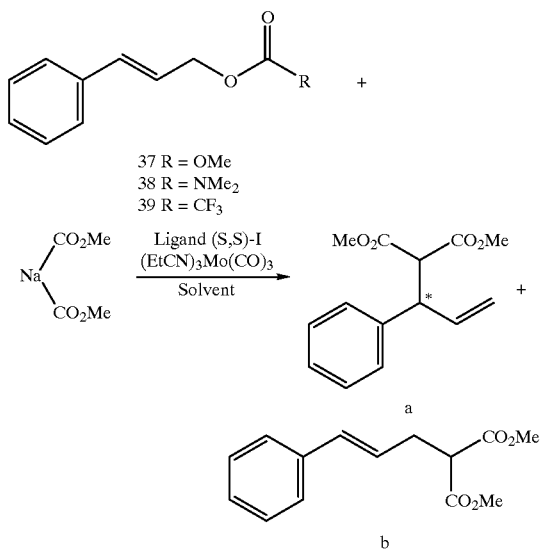

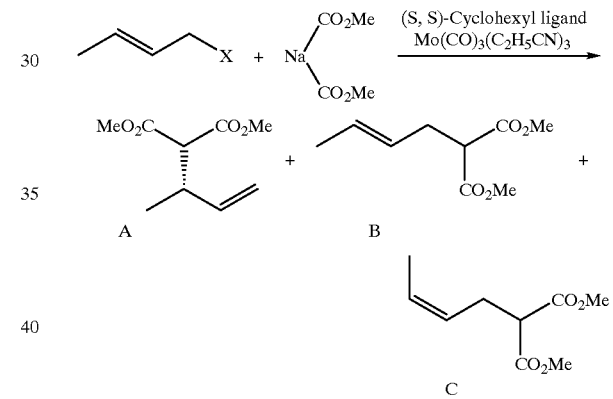

TABLE 10

Alkyl Substrate/Phosphate Leaving Groups

| Substrate | Mo mol % | Ligand mol % | Solvent | Temp | Time | Yield, % | A/B/C | e.e. of A, % |
|---|---|---|---|---|---|---|---|---|
| X = Cl | 10 | 15 | THF | 60° C. | 2 h | 76 | 2.1/1 (A/B + C) | 82 |
| X = Cl | 10 | 15 | THF | RT | 2 h | 65 | 1.9/1 (A/B + C) | 75 |
| X = Cl | 10 | 15 | THF/toluene | 60° C. | 5 h | 79 | 2.6/1 (A/B + C) | 79 |
| X = O(P = O)Ph$_2$ | 10 | 15 | THF | 65° C. | 4 h | 70 | 2.5/1/0.13 | 85 |
| X = O(P = O)(OEt)$_2$ | 10 | 15 | THF | 65° C. | 1 h | 82 | 4.4/1/0.17 | 89 |
| X = O(P = O)(OEt)$_2$ | 20 | 30 | THF | 65° C. | 1 h | 71 | 5.1/1/0.26 | 89 |
| X = O(P = O)(OPh)$_2$ | 10 | 15 | THF | 65° C. | 1 h | — | — | — |
| X = O(P = O)(OiPr)$_2$ | 10 | 15 | THF | 65° C. | 1 h | 72 | 5.7/1/0.19 | 93 |

Yields are isolated yields. Product C is generated by the competing uncatalyzed displacement reaction. Changing the leaving group from chloride to diphenyl phosphinate gave similar results, and the diphenyl phosphate substrate gave no reaction. Reaction of the diethyl phosphate, however, gave alkylated product with higher regioselectivity as well as good enantioselectivity. Use of a large amount of catalyst (20 mol %), or a bulkier leaving group, diisopropyl phosphate (last entry), reduced competition from the uncatalyzed $S_N2$ reaction and gave still better results.

These results represent the most successful demonstration to date, in terms of regioselectivity and enantioselectivy, of allylic alkylation of an aliphatic allyl group. It should be noted that the reduction in regioselectivity in these reactions is believed to be primarily (if not exclusively) due to the competing uncatalyzed reaction, which is nonselective. The catalyzed reaction is still highly stereoselective, as shown by the high e.e. of the addition products A. Reaction of substrates having bulkier substituents, and/or having the leaving group at the secondary position of the allyl group (i.e. the 1 terminus) is expected to give improved results.

E. Nucleophile

An ongoing challenge in molybdenum catalyzed allylic alkylations has been the limited range of effective nucleophiles. To date, only malonates have given consistent results. In the present reaction, however, acyclic ketoesters also gave good results. Table 11, below, shows the results of alkylations using methyl acetoacetate in the present system.

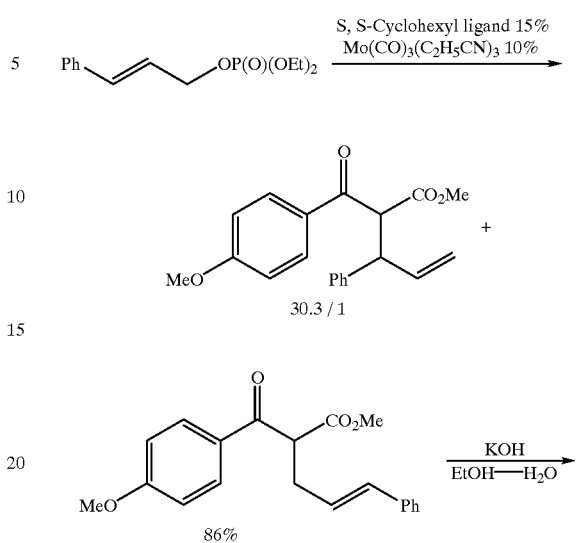

TABLE 11

Alkylations with methyl acetoacetate (acac)

| Substrate | Mo mol % | Ligand mol % | Solvent | Temp | Time | Yield, %[a] | A/B | ee of C, % |
|---|---|---|---|---|---|---|---|---|
| (a); X=OCO$_2$Me | 20 | 30 | THF | 65° C. | 18 h | 25 | >40/1 | — |
| (b); X=OCO$_2$Me | 10 | 15 | THF | 65° C. | 22 h | 47 (61) | >50/1 | 84 |
| (b); X=OCO$_2$Me | 20 | 30 | THF | 65° C. | 8 h | 66 (72) | 53/1 | 92 |
| (b); X=OCO$_2$Me | 10 | 15 | THF/toluene | 90° C. | 18 h | 54 (68) | 15/1 | — |
| (a); X=O(P=O)(OEt)$_2$ | 10 | 15 | THF | 65° C. | 20 h | 72 | 9.7/1 | 97 |
| (a); X=O(P=O)(OEt)$_2$ | 20 | 30 | THF | 65° C. | 4 h | 85 | 46/1 | 98 |

[a]Isolated yield; yields in parentheses are based on recovered starting material.

Substrates having a phosphate leaving group (e.g. cinnamyl phosphate) showed greater reactivity with the acac nucleophile, but also showed increased product from the uncatalyzed reaction. When increased catalyst (20 mol %) was used, the amount of competing product decreased, and regioselectivity was improved.

The ketoester methyl 4-methoxy-benzoylacetate (below) reacted with cinnamyl phosphate to give a 1:1 diastereomeric mixture of allylic alkylation product in good regioselectivity. Enantioselectivity was determined, after decarboxylation of the compound, to be >99%.

-continued

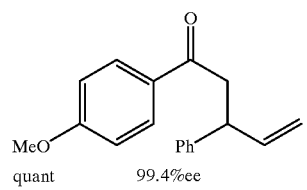

Substituted malonates can also be used in the present reaction. For example, reaction of carbonate 40 with dimethyl sodio methylmalonate gave, after hydrolysis and decarboxylation, acid 42 (most probably as a diastereoisomeric mixture at position 2), the methyl ester of which is methyl mantolinate, a monoterpene constituent of *Artemesia tridentada tridentada*.

the alkylation product 45 at 150° C. in toluene (sealed tube) for 48 hours gave a 73% yield of a product tentatively identified as the Diels-Alder adducts 46, as a mixture of three isomers in a 49:44:7 ratio, as determined by integration of the $^1$H NMR methoxycarbonyl signals. (Apparently one of the four theoretically possible Diels-Alder adducts was not formed).

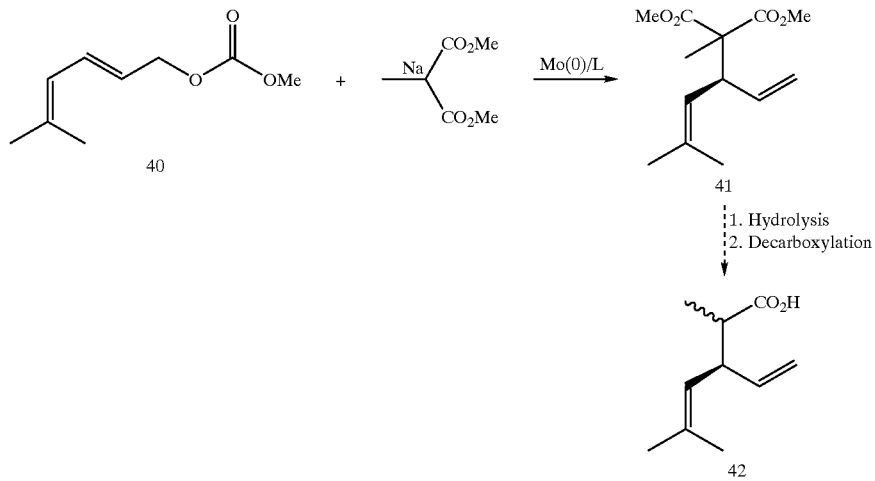

IV. Intramolecular Diels-Alder Reactions

Figure 5:
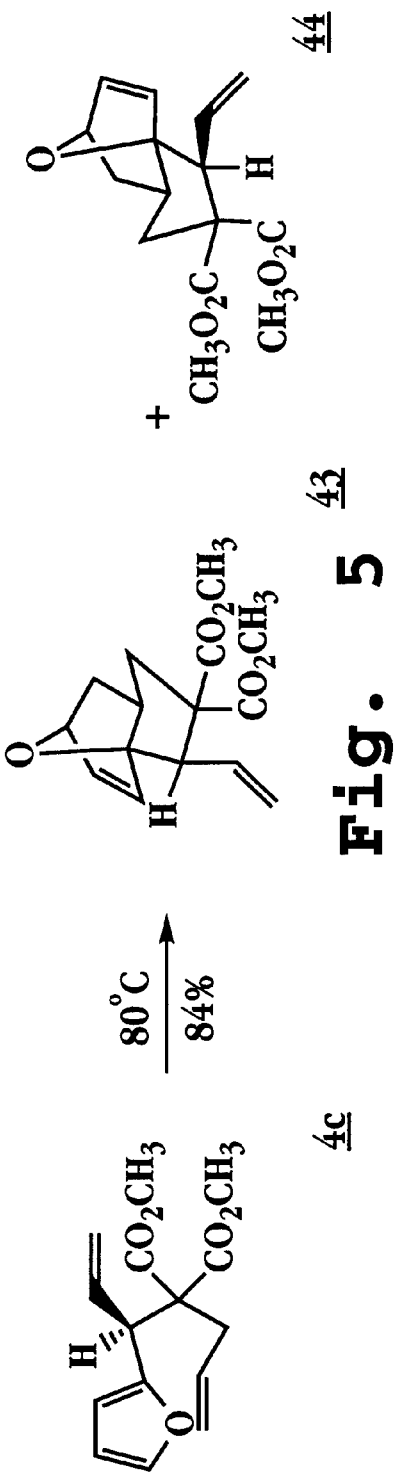
FIG. 5 illustrates the intramolecular Diels-Alder reaction of the product of reaction 14, Table 1, which was prepared according to the method of the invention.

The usefulness of the present stereo- and regioselective alkylation reaction was further demonstrated by subsequent Diels-Alder reaction, shown in FIG. 5, of the alkylation product of reaction 14, Table 1, predominantly 4c (R=allyl). Heating the product at 80° C. in 5:2 water:ethanol gave the diastereomeric Diels-Alder adducts 43 and 44 (FIG. 5) in a 3:1 ratio, each of which had an e.e. of 98%, as determined by chiral HPLC.

In another example, Mo-catalyzed reaction of methyl cinnamyl carbonate with dimethyl (2E,4E)-hexadienyl malonate afforded the branched product 45 in 60% yield with very good enantioselectivity (>94% ee) (see below). Heating

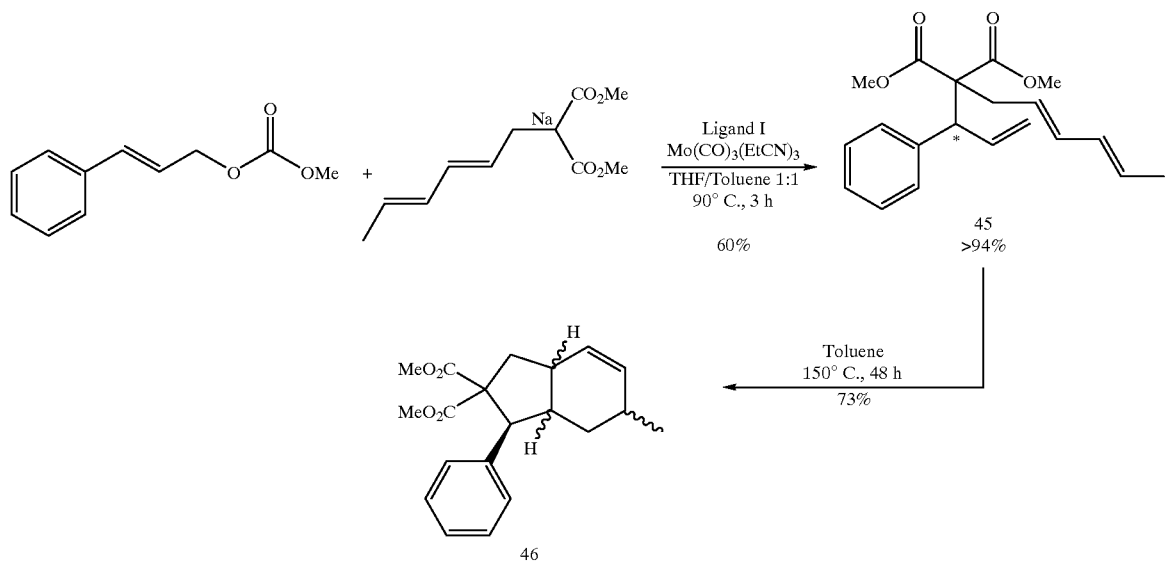

As a further example, when substrate 26, below, was reacted with dimethyl allylmalonate, a 5:1 mixture of two compounds was obtained (below). The branched isomer 47 was isolated in pure form in 71% yield. Heating 47 at 150° C. in toluene (sealed tube) for 15 hours afforded a product tentatively identified as the Diels-Alder adducts 48, as a mixture of four isomers in a 3:3:1:1 ratio, as determined by integration of the $^1$H NMR methoxycarbonyl signals.

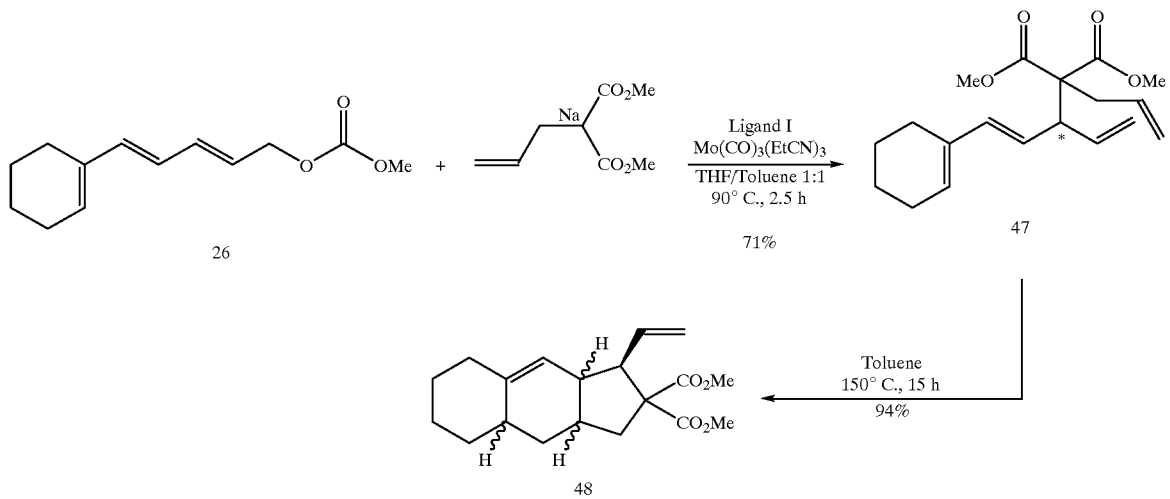

V. Advantages

The present reaction displays high selectivity over a wide temperature range, suggesting a fairly rigid chiral active site. The regioselectivity observed for attack at the more substituted terminus is generally significantly higher than with earlier achiral molybdenum catalysts. For example, as noted previously, previous molybdenum-catalyzed alkylations with dimethyl methylmalonate and cinnamyl substrates (Trost & Lautens, 1982, 1987, Trost & Merlic, 1990) normally led to attack at the less substituted allyl terminus. With the chiral ligands described herein, on the other hand, good selectivity for attack at the more substituted terminus is seen for a wide range of substrates.

The rate of reaction is also significantly improved compared to earlier molybdenum catalysts, where reaction typically required heating at reflux for 24 h or more (Trost & Lautens, 1982, 1987, Trost & Merlic, 1990, Merlic, 1988). Chiral ligands employed in Merlic (1988) also gave low e.e.'s in the product. In contrast, the reactions reported herein typically proceed in 2–3 h at reflux and less than 24 h at room temperature, and give high enantioselectivity.

The reaction also shows great versatility in terms of substrate, as shown above, giving good results with polyenes, halogenated substrates, various aryl substrates, and unprecedented success with non-aromatic substrates. The selectivity and versatility of the reaction make the method ideal for the synthesis of pharmaceutical compounds, or compounds employed as intermediates in the synthesis of pharmaceutical compounds. The method is also applicable to preparing other biologically active compounds where chirality is important to activity.

EXAMPLES

The following examples are intended to illustrate but not in any way limit the invention.

Materials and Methods

All reactions were carried out in flame-dried flasks or test tubes under a positive pressure of nitrogen. Solvents were generally distilled prior to use and transferred via syringe to the reaction vessel. $^1$H NMR and $^{13}$C NMR spectra were recorded on Varian Gemini-200 or 300. Optical Rotations were determined using a JASCO DIP-1000 polarimeter and were measured in 50 mm cells at 25±2° C. Infrared (IR) spectra [cm$^{-1}$] were obtained using a Perkin-Elmer FT-IR spectrometer. Melting points (mp) were determined in open capillary tubes using a Thomas-Hoover apparatus and are uncorrected. Thin-layer chromatography (TLC) was performed on precoated glass plates (Merck). Flash chromatography was performed by the method of Still (Still, et al., 1978) using silica gel 60, 230–400 mesh. The enantiomeric excess was determined by analytical, enantio-selective HPLC using the following columns with chiral stationary phases: Daicel Chiralcel® OD, Daicel Chiralpak® AD, and Daicel Chiralcel® OJ. *Unless otherwise indicated, reported e.e. refers to major isomer. Solvent systems, flow rates (in mLmin$^{-1}$) and retention times (in min) are always indicated; UV-detection (220 nm). High-resolution Mass spectra were provided by the Mass Spectronomy Facility of the School of Pharmacy (University of California, San Francisco) and combustion analyses were performed by M-H-W Laboratories, Phoenix, Ariz.

Synthesis of Substrates

Substrates were synthesized according to published procedures or using standard synthetic methods well known in the art. Reactions frequently employed were addition of vinylmagnesium bromide to aldehydes (e.g. Hammen et al., 1991), the Wadsworth-Horner-Emmons reaction of aldehydes with triethylphosphonoacetate, and DIBAL-H reduction of unsaturated ethyl esters. The method of Hung, 1984, was used for the preparation of allylic carbonates.

Mo-Catalyzed Alkylation Reactions

All reactions were performed in degassed (with nitrogen or argon) solvents. The ratio of the regioisomers (determined by $^1$H NMR) and the enantiomeric excess was determined from the isolated products. The absolute stereochemistry was assigned only in the cases where direct comparison of the optical rotation with literature values was possible. The $^1$H NMR data of the minor isomer were normally assigned with the assistance of a $^1$H NMR spectrum independently obtained by a palladium(0)-catalyzed reaction. In the palladium reactions the linear trans-isomer was always the major product, although with many substrates significant amount of its cis-isomer and/or of the branched product were also formed.

Example 1

General procedure A; THF as solvent (Trost and Hachiya, 1998). A solution of Mo(CO)$_3$(EtCN)$_3$ and ligand in THF was heated at 60–70° C. for 1 h. A solution of sodiomalonate (prepared by adding the malonate to sodium hydride (60% dispersion in oil; purchased from Aldrich)) and the substrate in THF was added dropwise via syringe at 60° C. and the mixture was heated at 70° C. for the time indicated. The reaction mixture was diluted with ether (5 mL) and water (5 mL) was added. The layers were separated and the aqueous layer was extracted with ether (3×10 mL). The combined organic layers were washed with brine (10 mL), dried over magnesium sulfate and the solvent removed in vacuo. Flash chromatography (with the solvent system indicated) afforded the pure product as a mixture of the two regioisomers.

Example 2

General procedure B; Toluene/THF 1:1 as solvent. A solution of $Mo(CO)_3(EtCN)_3$ and ligand in toluene was heated at 60–70° C. for 1 h. A solution of sodiomalonate (prepared by adding the malonate to sodium hydride (60% dispersion in oil)) and the substrate in THF was added dropwise via syringe at 60° C. and the mixture was heated at 80–90° C. for the time indicated. The reaction mixture was diluted with ether (5 mL) and water (5 mL) was added. The layers were separated and the aqueous layer was extracted with ether (3×10 mL). The combined organic layers were washed with brine (10 mL), dried over magnesium sulfate and the solvent removed in vacuo. Flash chromatography (with the solvent system indicated) afforded the product as a mixture of the two regioisomers.

Examples 3A–3D

Preparation of (S)-Methyl 2-Methoxycarbonyl-3-phenyl-4-pentenoate and Methyl (E)-2-methoxycarbonyl-5-phenyl-4-pentenoate (Lloyd-Jones and Pfalz, 1995; Trost and Hachiya, 1998; Hung, 1984).

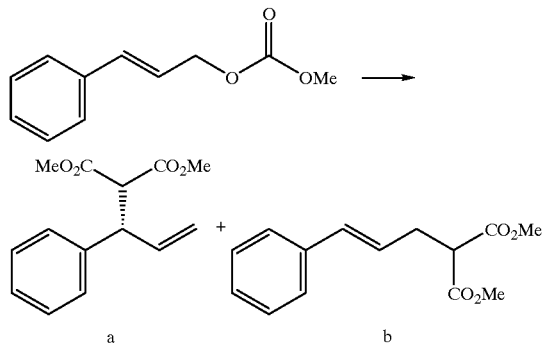

A. Mo-Catalyzed Alkylation with Pyrrolidine Ligand III:

According to procedure A with $Mo(CO)_3(EtCN)_3$ (13.0 mg, 0.038 mmol) and ligand III (21.9 mg, 0.056 mmol) in 1.5 mL THF and carbonate (72.4 mg, 0.34 mmol), dimethyl malonate (109.4 mg, 0.83 mmol) and sodium hydride (30.0 mg, 0.75 mmol) in 1.5 mL THF. The reaction mixture was heated at 70° C. for 18 h. Work-up and flash chromatography (petroleum ether/ether 6:1) afforded 20 mg recovered starting material and 37 mg (40%; 55% brsm) of a colorless oil consisting of a mixture of regioisomers; a/b 82:18. $[\alpha]_D$=−27.1 (c 1.43, $CHCl_3$). 94% ee.

B. According to procedure B with $Mo(CO)_3(EtCN)_3$ (9.0 mg, 0.026 mmol) and ligand III (15.7 mg, 0.039 mmol) in 1.3 mL toluene and carbonate (50.1 mg, 0.26 mmol), dimethyl malonate (75.8 mg, 0.57 mmol) and sodium hydride (20.9 mg, 0.52 mmol) in 1.3 mL THF. The reaction mixture was heated at 90° C. for 8 h. Work-up and flash chromatography (petroleum ether/ether 6:1) afforded 15 mg recovered starting material and 49.0 mg (76%; 98% brsm) of a colorless oil consisting of a mixture of regioisomers; a/b 89:11. $[\alpha]_D$=−25.0 (c 1.53, $CHCl_3$). 94% ee.

C. Mo-Catalyzed Alkylation with Diphenyl Ligand II:

According to procedure A with $Mo(CO)_3(EtCN)_3$ (8.3 mg, 0.024 mmol) and ligand II (15.2 mg, 0.036 mmol) in 1.5 mL THF and carbonate (46.0 mg, 0.24 mmol), dimethyl malonate (69.0 mg, 0.53 mmol) and sodium hydride (19.0 mg, 0.22 mmol) in 1 mL THF. The reaction mixture was heated at 70° C. for 8 h. Work-up and flash chromatography (petroleum ether/ethyl acetate 20:1) afforded 8.0 mg recovered starting material and 43.9 mg (74%; 89% brsm) of a colorless oil consisting of a mixture of regioisomers; a/b 92:8. $[\alpha]_D$=−32.9 (c 2.00, $CHCl_3$) 98% ee.

D. According to procedure B with $Mo(CO)_3(EtCN)_3$ (7.8 mg, 0.023 mmol) and ligand II (14.3 mg, 0.034 mmol) in 1.5 mL toluene and carbonate (43.8 mg, 0.23 mmol), dimethyl malonate (66.4 mg, 0.50 mmol) and sodium hydride (18.3 mg, 0.46 mmol) in 1 mL THF. The reaction mixture was heated at 90° C. for 3 h. Work-up and flash chromatography (petroleum ether/ethyl acetate 20:1) afforded 53.8 mg (95%) of a colorless oil consisting of a mixture of regioisomers; a/b 95:5 $[\alpha]_D$=−34.5 (c 1.92, $CHCl_3$). 99% ee.

Example 4

Preparation of Dimethyl 2-(1-phenyl-allyl)-malonate using ligand IV

Cycloheptyl ligand IV (10.2 mg, 0.030 mmol) and $Mo(CO)_3(C_2H_5CN)_3$ (6.9 mg, 0.020 mmol) were dissolved in 1.0 ml of THF at rt. The reaction mixture was heated at 60° C. for 1 h. After cooling to rt, 1.0 ml of THF solution of sodium dimethylmalonate enolate, prepared from dimethyl malonate (58.0 mg, 0.44 mmol) and sodium hydride (10.2 mg, 0.40 mmol) in tetrahydrofuran, and methyl 3-phenyl-2-propenyl carbonate were added successively. The reaction mixture was heated at 65° C. for 8 h. The reaction mixture was poured into water and extracted with ethyl acetate. The combined organic layers were dried over sodium sulfate, and the solvent was removed under reduced pressure. The ratio of 1,1-dimethoxycarbonyl-2-phenyl-3-butene and linear compound was determined by $^1$H NMR (400 MHz) to be 34.2/1. The residue was chromatographed on silica (⅛ ethyl acetate/petroleum ether, Rf=0.3) to yield the mixture of branched and linear compound (36.7 mg, 74%). $[\alpha]_D$−29.7° (c 1.27, $CHCl_3$); 99% ee.

Examples 5A–B

Preparation of dimethyl 2-(1-thiophene-2-yl-allyl)-malonate using ligands IV and VIII Cycloheptyl ligand IV (10.2 mg, 0.030 mmol) and $Mo(CO)_3(C_2H_5CN)_3$ (6.9 mg, 0.020 mmol) were dissolved in 1.0 ml of THF at rt. The reaction mixture was heated at 60° C. for 1 h. After cooling to rt., 1.0 ml of THF solution of sodium dimethylmalonate enolate, prepared from dimethyl malonate (58.0 mg, 0.44 mmol) and sodium hydride (10.2 mg, 0.40 mmol) in tetrahydrofuran, and methyl 1-(2-thienyl)-2-propenyl carbonate were added successively. The reaction mixture was heated at 65° C. for 4.5 h. The reaction mixture was poured into water and extracted with ethyl acetate. The combined organic layers were dried over sodium sulfate, and the solvent was removed under reduced pressure. The ratio of dimethyl 2-(1-thiophene-2-yl-allyl)- malonate and linear compound was determined by ¹H NMR (400 MHz) to be 16.0/1. The residue was chromatographed on silica (1/7 ethyl acetate/petroleum ether, Rf=0.3) to yield the mixture of branched and linear compound. (40.3 mg, 78%) $[\alpha]_D$-31.1° (c 1.35, CHCl$_3$); 92% e.e. for major isomer.

When the reaction was repeated using ligand VIII, the regioisomer ratio of the product, obtained in 83% yield, was was determined to be 12.7/1. $[\alpha]_D$+30.2°; 84% e.e. for major isomer.

Example 6

Preparation of Methyl (4E)-2-Methoxycarbonyl-5-phenyl-3-vinyl-4-pentenoate 12a and Methyl (4E,6E)-2-Methoxycarbonyl-7-phenyl-4,6-heptadienoate 12b

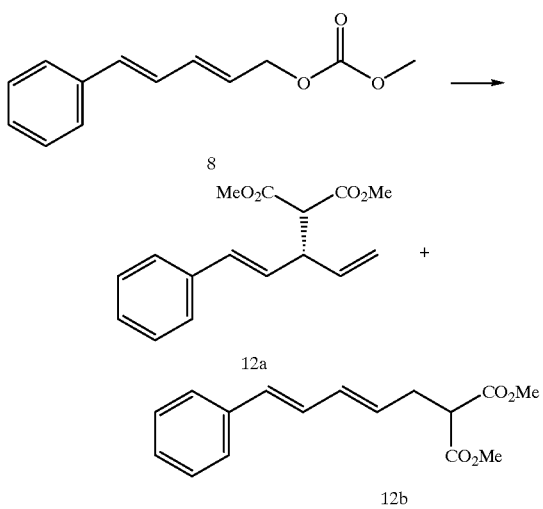

According to procedure B with Mo(CO)$_3$(EtCN)$_3$ (6.4 mg, 0.0188 mmol) and ligand IV (11.7 mg, 0.0282 mmol) in 1 mL toluene and carbonate 8 (40.5 mg, 0.185 mmol), dimethyl malonate (53.9 mg, 0.41 mmol) and sodium hydride (14.8 mg, 0.37 mmol) in 1 mL THF. The reaction mixture was heated at 90° C. for 3 h. Work-up and flash chromatography (petroleum ether/ether 10:1) afforded 48.5 mg (95%) of 12 as a colorless oil consisting of a mixture of regioisomers; 12a/12b 86:14 $[\alpha]_D$=-15.7 (c 2.51, CHCl$_3$). 98% ee, major isomer.

Examples 7A–7B

Preparation of Methyl (4E,6E)-2-Methoxycarbonyl-7-phenyl-3-vinyl-4,6-heptadienoate 13a and Methyl (4E,6E,8E)-2-Methoxycarbonyl-9-phenyl-4,6,8-nonatrienoate 13b

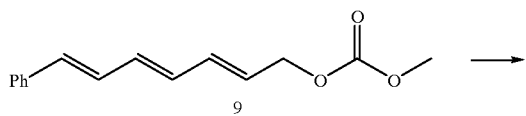

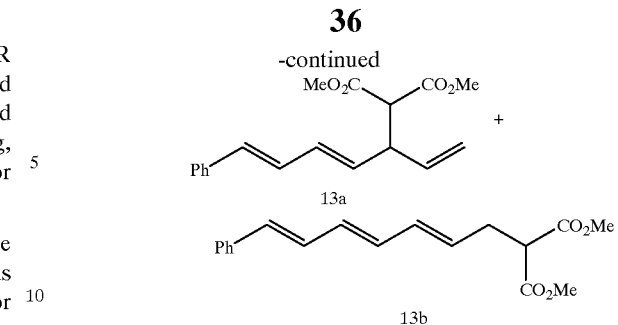

A. According to procedure B with Mo(CO)$_3$(EtCN)$_3$ (3.1 mg, 0.009 mmol) and ligand II (5.7 mg, 0.014 mmol) in 0.7 mL toluene and carbonate 9 (21.9 mg, 0.090 mmol), dimethyl malonate (26.1 mg, 0.198 mmol) and sodium hydride (7.2 mg, 0.180 mmol) in 0.7 mL THF. The reaction mixture was heated at 90° C. for 4 h. Work-up and flash chromatography (petroleum ether/ether 6:1) afforded 8.1 mg of starting material and 15.6 mg (58%; 92% brsm) of 13 as a colorless oil consisting of a mixture of regioisomers; 13a/13b 84:16. $[\alpha]_D$=-42.1 (c 0.51, CH$_2$Cl$_2$). 97% ee.

B. According to procedure B with Mo(CO)$_3$(EtCN)$_3$ (5.4 mg, 0.016 mmol) and ligand (R,R)-I (7.6 mg, 0.024 mmol) in 1 mL toluene and carbonate 9 (25.5 mg, 0.104 mmol), dimethyl malonate (30.2 mg, 0.23 mmol) and sodium hydride (8.4 mg, 0.21 mmol) in 1 mL THF. The reaction mixture was heated at 85° C. for 3.5 h. Work-up and flash chromatography (petroleum ether/ether 6:1) afforded 11.8 mg of starting material and 21.4 mg (68%; 94% brsm) of 13 as a colorless oil consisting of a mixture of regioisomers; 13a/13b 86:14. $[\alpha]_D$=-44.9 (c 0.40, CH$_2$Cl$_2$). >99% ee.

Example 8

Preparation of Methyl (4E)-2-Methoxycarbonyl-4-methyl-3-vinyl-4-hexenoate 21a and Methyl (4E,6E)-2-Methoxycarbonyl-6-methyl-4,6-octadienoate 21b

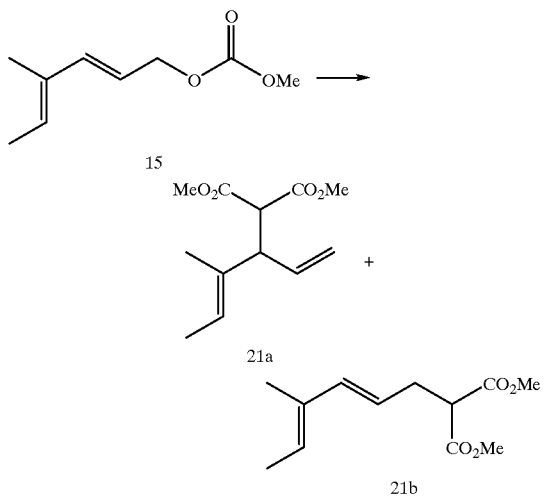

According to procedure B with Mo(CO)$_3$(EtCN)$_3$ (7.5 mg, 0.022 mmol) and ligand (R,R)-I (10.7 mg, 0.035 mmol) in 1 mL toluene and carbonate 15 (37.0 mg, 0.217 mmol), dimethyl malonate (63.2 mg, 0.48 mmol) and sodium hydride (17.4 mg, 0.44 mmol) in 1 mL THF. The reaction mixture was heated at 90° C. for 3 h. Work-up and flash chromatography (petroleum ether/ether 8:1) afforded 43.8 mg (89%; 94% brsm) of 21 as a colorless oil consisting of a mixture of regioisomers; 21a/21b 98:2 [α]$_D$=+10.3 (c 0.06, CH$_2$Cl$_2$). 98% ee.

Example 9

Preparation of Methyl 3-(1-Cyclopenten-1-yl)-2-methoxycarbonyl-4-pentenoate 23a and Methyl (E)-5-(1-Cyclopenten-1-yl)-2-methoxycarbonyl-4-pentenoate 23b

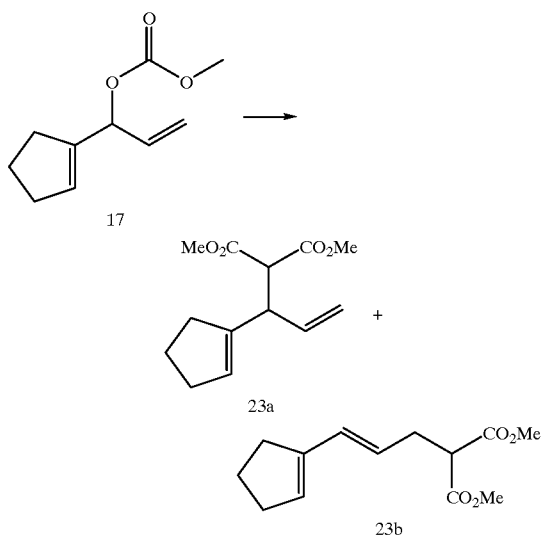

According to procedure B with Mo(CO)$_3$(EtCN)$_3$ (10.5 mg, 0.030 mmol) and ligand (R,R)-I (14.8 mg, 0.046 mmol) in 1.5 mL toluene and carbonate 17 (58.4 mg, 0.32 mmol), dimethyl malonate (88.4 mg, 0.67 mmol) and sodium hydride (24.3 mg, 0.61 mmol) in 1.5 mL THF. The reaction mixture was heated at 90° C. for 2 h. Work-up and flash chromatography (petroleum ether/ether 10:1) afforded 72.0 mg (94%) of 23 as a colorless oil consisting of a mixture of regioisomers; 23a/23b 92:8. [α]$_D$=−52.1 (c 3.15, CH$_2$Cl$_2$) .87% ee.

Example 10

Preparation of Methyl 3-(2-Dihydropyranyl)-2-methoxycarbonyl-4-pentenoate 25a and Methyl (5E)-6-(2-Dihydropyranyl)-2-methoxycarbonyl-5-hexenoate 25b

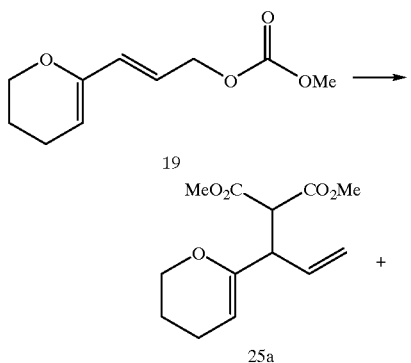

According to procedure B with Mo(CO)$_3$(EtCN)$_3$ (12.5 mg, 0.036 mmol) and ligand (R,R)-I (17.6 mg, 0.054 mmol) in 1.8 mL toluene and carbonate 19 (35.9 mg, 0.18 mmol), dimethyl malonate (52.6 mg, 0.40 mmol) and sodium hydride (14.5 mg, 0.36 mmol) in 1.0 mL THF. The reaction mixture was heated at 90° C. for 1.5 h. Work-up and flash chromatography (petroleum ether/ether 6:1) afforded 42.8 mg (93%) of 25 as a colorless oil consisting of a mixture of regioisomers; 25a/25b 93:7. [α]$_D$=−11.9 (c 2.00, CH$_2$Cl$_2$). 96% ee.

Example 11

Methyl (4E,6E)-2-Methoxycarbonyl-3-vinyl-4,6-octadienoate 29a and Methyl (4E,6E,8E)-2-Methoxycarbonyl-4,6,8-decatrienoate 29b

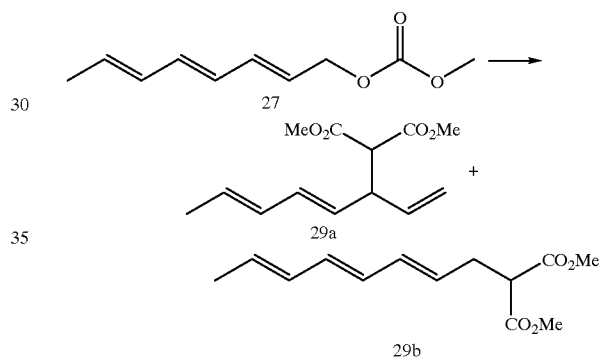

According to procedure B with Mo(CO)$_3$(EtCN)$_3$ (9.8 mg, 0.028 mmol) and ligand (R,R)-I (13.8 mg, 0.043 mmol) in 1.5 mL toluene and carbonate 27 (51.7 mg, 0.28 mmol), dimethyl malonate (82.5 mg, 0.63 mmol) and sodium hydride (22.7 mg, 0.57 mmol) in 1.5 mL THF. The reaction mixture was heated at 85° C. for 3 h. Work-up and flash chromatography (petroleum ether/ether 8:1) afforded besides 2.5 mg starting material 54.5 mg (81%; 85% brsm) of 29 as a colorless oil consisting of a mixture of regioisomers; 29a/29b 91:9. [α]$_D$=−15.0 (c 2.00, CH$_2$Cl$_2$). 98% ee.

Examples 12A–B.

Preparation of Methyl 2-Methoxycarbonyl-5-phenyl-3-vinyl-4-pentynoate 31a and Methyl (4E)-2-Methoxycarbonyl-7-phenyl-hept-4-en-6-ynoate 31b

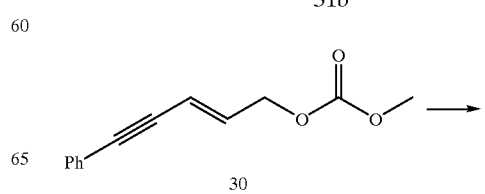

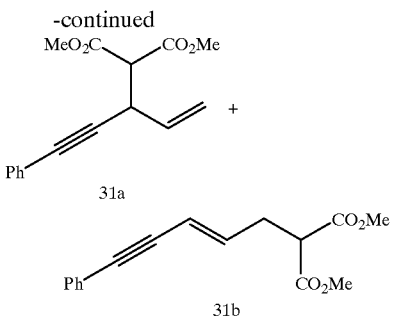

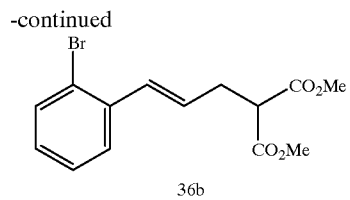

A. According to procedure B with Mo(CO)₃(EtCN)₃ (6.2 mg, 0.018 mmol) and ligand (R,R)-I (8.7 mg, 0.027 mmol) in 1 mL toluene and carbonate 30 (36.4 mg, 0.17 mmol), dimethyl malonate (52.2mg, 0.40 mmol) and sodium hydride (14.4 mg, 0.36 mmol) in 1.0 mL THF. The reaction mixture was heated at 85° C. for 2.5 h. Work-up and flash chromatography (petroleum ether/ether 8:1) afforded besides 5 mg starting material 37.6 mg (82%; 95 brsm) of 31 as a colorless oil consisting of a mixture of regioisomers; 31a/31b 84:16. [α]$_D$=−86.6 (c 1.40, CH$_2$Cl$_2$). 99% ee.

B. Pd-catalyzed reaction: To solution of Pd$_2$(dba)$_3$.CHCl$_3$ (9.5 mg, 0.0092 mmol) and triphenylphosphine (12.1 mg, 0.046 mmol) in 2 mL THF was added a solution of 30 (39.8 mg, 0.184 mmol) and dimethyl malonate (48.7 mg, 0.37 mmol) in 2 mL THF. After 2 h at r.t. the mixture was diluted with ether (5 mL) and water (5 mL) was added. The layers were separated and the aqueous layer was extracted with ether (3×10 mL). The combined organic layers were washed with brine (10 mL), dried over magnesium sulfate the solvent removed in vacuo. Flash chromatography (petroleum ether/ether 8:1) afforded 48.0 mg (96%) of a mixture of 31b and 31c in a ratio of 58:42.

Example 13

Preparation of Methyl 3-(2-Bromophenyl)-2-methoxycarbonyl-4-pentenoate 36a and Methyl (E)-5-(2-Bromophenyl)-2-methoxycarbonyl-4-pentenoate 36b.

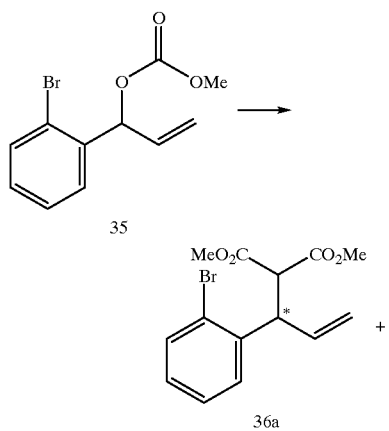

According to procedure B with Mo(CO)₃(EtCN)₃ (4.8 mg, 0.0139 mmol) and ligand (S,S)-I (6.8 mg, 0.021 mmol) in 0.6 mL toluene and carbonate 35 (37.7 mg, 0.14 mmol), dimethyl malonate (40.4 mg, 0.306 mmol) and sodium hydride (11.1 mg, 0.28 mmol) in 0.8 mL THF. The reaction mixture was heated at 90° C. for 3 h. Work-up and flash chromatography (petroleum ether/ethyl acetate 10:1) afforded 43.5 mg (96%) of 36 as a colorless oil consisting of a mixture of regioisomers; 36a/36b 96:4. [α]$_D$=+42.5 (c 2.60, CH$_2$Cl$_2$). 91% ee.

Example 14

Preparation of Methyl 2-Methoxycarbonyl-3-phenyl-4-pentenoate a and Methyl (E)-2-Methoxycarbonyl-5-phenyl-4-pentenoate b using a variety of leaving groups According to procedure B with Mo(CO)₃(EtCN)₃ (7.5 mg, 0.022 mmol) and ligand (S,S)-I (4.2 mg, 0.013 mmol) in 1 mL toluene and carbonate 37 (41.8 mg, 0.22 mmol), dimethyl malonate (62.9 mg, 0.48 mmol) and sodium hydride (17.3 mg, 0.44 mmol) in 1 mL THF. The reaction mixture was heated at 80° C. for 2 h. Work-up and flash chromatography (petroleum ether/ether 6:1) afforded 51.8 mg (96%) of a colorless oil consisting of a mixture of regioisomers; a/b 96:4. 99% ee.

According to procedure B with Mo(CO)₃(EtCN)₃ (7.6 mg, 0.022 mmol) and ligand (S,S)-I (10.7 mg, 0.039 mmol) in 1.0 mL toluene and carbamate 38 (45.0 mg, 0.22 mmol), dimethyl malonate (63.4 mg, 0.48 mmol) and sodium hydride (17.6 mg, 0.44 mmol) in 1 mL THF. The reaction mixture was heated at 90° C. for 24 h. Work-up and flash chromatography (petroleum ether/ether 6:1) afforded 41.0 mg (75%; 91% brsm) of a colorless oil consisting of a mixture of regioisomers; a/b 93:7. 99% ee.

According to procedure B with Mo(CO)₃(EtCN)₃ (3.0 mg, 0.0087 mmol) and ligand (S,S)-I (4.2 mg, 0.013 mmol) in 0.5 mL toluene and trifluoroacetate 39 (20.0 mg, 0.087 mmol), dimethyl malonate (25.1 mg, 0.19 mmol) and sodium hydride (7.0 mg, 0.17 mmol) in 0.8 mL THF. The reaction mixture was heated at 80° C. for 4 h. Work-up and flash chromatography (petroleum ether/ether 6:1) afforded 20.2 mg (94%) of a colorless oil consisting of a mixture of regioisomers; a/b 93:7. 99% ee.

Examples 15A–B

Preparation of Methyl 2-Methoxycarbonyl-5-(1-cyclohexen-1-yl)-3-vinyl-4-pentynoate 34a and Methyl (4E)-2-Methoxycarbonyl-7-(1-cyclohexen-1-yl)-hept-4-en-6-ynoate 34b using different leaving groups A. According to procedure B with Mo(CO)₃(EtCN)₃ (8.1 mg, 0.024 mmol) and ligand (R,R)-I (11.4 mg, 0.035 mmol) in 1.2 mL toluene and carbonate 32 (25.8 mg, 0.12 mmol), dimethyl malonate (34.1 mg, 0.26 mmol) and sodium hydride (9.4 mg, 0.24 mmol) in 1.0 mL THF. The reaction mixture was heated at 85° C. for 4.5 h. Work-up and flash chromatography (petroleum ether/ether 8:1) afforded besides 4.2 mg starting material 26.2 mg (81%; 97% brsm) of 34 as a colorless oil consisting of a mixture of regioisomers; 34a/34b 88:12. $[\alpha]_D=-63.9$ (c 1.25, $CH_2Cl_2$). 99% ee.

B. According to procedure B with $Mo(CO)_3(EtCN)_3$ (7.5 mg, 0.022 mmol) and ligand (R,R)-I (10.6 mg, 0.033 mmol) in 1 mL toluene and phosphate 33 (64.8 mg, 0.22 mmol), dimethyl malonate (63.2 mg, 0.48 mmol) and sodium hydride (17.4 mg, 0.44 mmol) in 1.0 mL THF. The reaction mixture was heated at 90° C. for 2 h. Work-up and flash chromatography (petroleum ether/ether 5:1) afforded 49.8 mg (82%; 95% brsm) of 34 as a colorless oil consisting of a mixture of regioisomers; 34a/34b 66:34. 96% ee.

Example 16

Reaction of methyl 3-(3-phenylpropenyl) carbonate with sodio methyl acetoacetate

S, S- ligand I (19.4 mg, 0.060 mmol) and $Mo(CO)_3$ $(C_2H_5CN)_3$ (13.8 mg, 0.04 mmol) were dissolved in 1.0 ml of tetrahydrofuran at rt, and the reaction mixture was heated at 60° C. for 1 h. After cooling to rt., a solution of sodio methyl acetoacetate in 1.0 ml of tetrahydrofuran, prepared from methyl acetoacetate (51.1 mg, 0.44 mmol) and sodium hydride (10.2 mg, 0.40 mmol) in tetrahydrofuran, and methyl 1-phenyl-allyl carbonate (38.6 mg, 0.201 mmol) were added successively. The reaction mixture was stirred at 65° C. for 8 h, poured into water and extracted with ethyl acetate. The combined organic layers were dried over sodium sulfate, and the solvent was removed under reduced pressure to give a mixture of branched products (the ratio of diastereomers was 1.2/1) and linear product. The ratio of methyl 2-acetyl-3-phenyl-pent-4-enoate and linear compound was determined to be 52.8/1 by $^1H$ NMR (400 MHz). The residue was chromatographed on silica (1/8 ethyl acetate/petroleum ether, Rf=0.3) to yield the mixture of diastereomers and linear compound. (30.6 mg, 66%, 72% BRSM) $[\alpha]_D$+28.7° (c 1.21, $CHCl_3$)

Example 17

Reaction of Cinnamyl Diethyl Phosphate with Sodio Methyl Acetoacetate Using 20 mol % Catalyst S, S-ligand I (19.4 mg, 0.060 mmol) and $Mo(CO)_3$ $(C_2H_5CN)_3$ (13.8 mg, 0.04 mmol) were dissolved in 1.0 ml of tetrahydrofuran at rt., and the reaction mixture was heated at 60° C. for 1 h. After cooling to rt., a solution of sodio methyl acetoacetate in 1.0 ml of tetrahydrofuran, prepared from methyl acetoacetate (51.1 mg, 0.44 mmol) and sodium hydride (10.1 mg, 0.40 mmol) in tetrahydrofurane and cinnamyl diethyl phosphate (54.2 mg, 0.201 mmol) were added successively. The reaction mixture was stirred at 65° C. for 4 h,, poured into water and extracted with ethyl acetate. The combined organic layers were dried over sodium sulfate, and the solvent was removed under reduced pressure to give a mixture of branched products (diastereomeric ratio 1.2/1) and linear product. The ratio of methyl 2-acetyl-3-phenyl-pent-4-enoate and linear compound was determined to be 45.7/1 by $^1H$ NMR (400 MHz). The residue was chromatographed on silica (1/8 ethyl acetate/petroleum ether, Rf=0.3) to yield a mixture of diastereomers and linear compound. (39.8 mg, 85%) $[\alpha]_D$+33.6° (c 1.38, $CHCl_3$)

Example 18

Methyl 2-(4-methoxy-benzoyl)-3-phenyl-pent-4-en-1-one

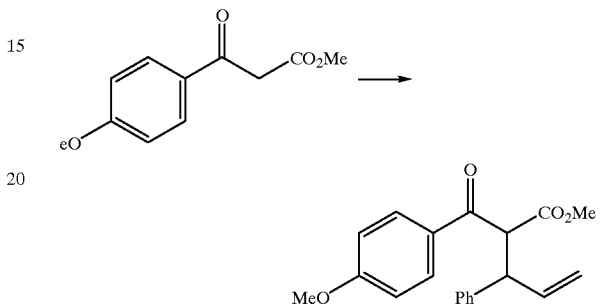

S, S-ligand I (9.7 mg, 0.030 mmol) and $Mo(CO)_3$ $(C_2H_5CN)_3$ (6.9 mg, 0.020 mmol) were reacted with sodio methyl 4-methoxy-benzoacetate, prepared from methyl 4-methoxy-benzoacetate (92 mg, 0.44 mmol) and sodium hydride (10.1 mg, 0.40 mmol), cinnamyl diethyl phosphate (54.1 mg, 0.200 mmol) as described for Examples 16 and 17. The reaction yielded a mixture of branched products (diastereomeric ratio 1/1) and linear product. The ratio of methyl 2-(4-methoxy-benzoyl)-3-phenyl-pent-4-en-1-one and linear compound was determined to be 30.3/1 by $^1H$ NMR (400 MHz). Purification gave 55.6 mg (86%) $[\alpha]_D$+ 65.8° (c 1.00, $CHCl_3$).

Examples 19A–B

Alkylation of 1-(2-furyl)-2-propenyl acetate with dimethyl sodioallylmalonate and subsequent Diels-Alder reaction A. A solution of $(C_2H_5CN)_3Mo(CO)_3$ (14.2 mg, 0.0411 mmol) and chiral ligand I (19.9 mg, 0.0613 mmol) in THF (2.0 mL) was stirred at 60° C. for 1 h. A solution of dimethyl sodioallylmalonate, 3c (prepared from dimethyl allylmalonate (149 mg, 0.865 mmol) and 60% NaH (32.0 mg, 0.800 mmol) in THF (2.0 mL)) and 1-(2-furyl)-2-propenyl acetate, 2b (68.0 mg, 0.410 mmol) were successively added at room temperature. The mixture was stirred at room temperature for 12 h. Water (4 mL) was added to quench the reaction at room temperature. The mixture was extracted with diethyl ether (15 mL×3). The combined organic layer was washed with brine (10 mL×1) and dried ($MgSO_4$). The solvents were evaporated in vacuo, and the residue was purified by chromatography on silica gel (petroleum ether/ethyl acetate) to give the mixture of 4 and 5 (57.0 mg, 50% yield, 4:5=99:1).

B. The mixture of 4c and 5c (predominantly 4c) generated in Example 19A was stirred at 80° C. in ethanol-water (9.8 ml, 2:5) for 44 h. The mixture was cooled and extracted with diethyl ether (15 ml×3), and the combined organic layer was washed with brine (10 ml×1) and dried ($MgSO_4$). The solvents were evaporated in vacuo, and the residue was purified by chromatography on silica gel (petroleum ether/ ethyl acetate=30/1-20/1-10/1) to give the mixture of 43 and 44 (44.4 mg, 79% yield (84% yield based on the recovered starting material), 43:44=76:24). The enantiomeric excesses were determined after isolating 43 and 44 by chromatography on silica gel (petroleum ether/ethyl acetate=30/1-20/1), respectively.

Diels-Alder Adduct 43 (major): $[\alpha]^{24.8}{}_D=-182°$ (c 2.09, CHCl$_3$). $^1$H NMR (300 MHz, CDCl$_3$): δ 6.38 (d, J=5.8 Hz, 1H), 6.29 (dd, J=5.8, 1.6 Hz, 1H), 5.73 (dt, J=17.1, 10.0 Hz, 1H), 5.25 (dd, J=17.1, 2.0 Hz, 1H), 5.15 (dd, J=10.0, 2.0 Hz, 1H), 5.04 (dd, J=4.4, 1.6 Hz, 1H), 4.02 (d, J=10.0 Hz, 1H), 3.76 (s, 3H), 3.66 (s, 3H), 2.45 (d, J=5.8 Hz, 1H), 2.42 (d, J=2.5 Hz, 1H), 1.72–1.79 (m, 2H), 1.44 (dd, J=11.2, 8.2 Hz, 1H). $^{13}$C NMR (75 MHz, CDCl$_3$): δ 172.9, 169.8, 136.5, 136.4, 132.9, 118.8, 98.9, 80.1, 67.1, 52.9, 52.2, 49.3, 41.6, 38.9, 32.4. Diels-Alder Adduct 44 (minor): $[\alpha]^{26.0}{}_D=-47.7°$ (c 0.57, CHCl$_3$). $^1$H NMR (300 MHz, CDCl$_3$): δ 6.28–6.32 (m, 2H), 5.69 (dt, J=17.0, 10.2 Hz, 1H), 5.34 (dd, J=17.0, 1.8 Hz, 1H), 5.23 (dd, J=10.2, 1.8 Hz, 1H), 4.98 (d, J=3.9 Hz, 1H), 3.90 (d, J=10.2 Hz, 1H), 3.74 (s, 3H), 3.67 (s, 3H), 2.88 (dd, J=13.7, 9.1 Hz, 1H), 2.20–2.27 (m, 1H), 2.06 (dd, J=13.7, 8.4 Hz, 1H), 1.70–1.76 (m, 1H), 1.54 (dd, J=11.5, 7.7 Hz, 1H). $^{13}$C NMR (75 MHz, CDCl$_3$): δ 171.8, 171.0, 136.3, 134.3, 133.7, 119.8, 99.9, 79.7, 67.6, 52.7, 52.4, 51.2, 41.8, 38.0, 34.6.

Examples 20A–B

Preparation of methyl (4E,6E)-2-methoxycarbonyl-2-[(1-phenyl)-2-propen-1-yl]-4,6-octadienoate 45 and subsequent Diels-Alder Reaction

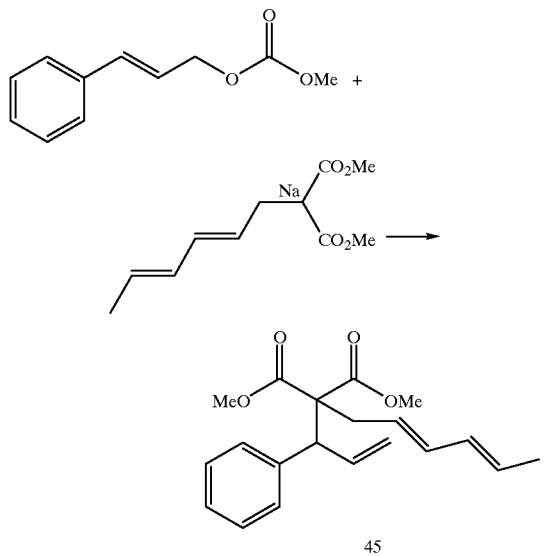

45

A. According to procedure B with Mo(CO)$_3$(EtCN)$_3$ (10.4 mg, 0.030 mmol) and ligand (R,R)-I (14.7 mg, 0.045 mmol) in 1.5 mL toluene and methyl cinnamyl carbonate (57.9 mg, 0.30 mmol), dimethyl (2E, 4E)-2,4-hexadienyl malonate [46] (140.7 mg, 0.66 mmol) and sodium hydride (24.1 mg, 0.61 mmol) in 1.5 mL THF. The reaction mixture was heated at 90° C. for 3 h. Work-up and flash chromatography (petroleum ether/ether 12:1) afforded 59.1 mg (60%) of the malonate adduct 45 as a colorless oil (isomeric purity>94:6; $^1$H NMR). $[\alpha]_D=-2.0$ (c 2.21, CH$_2$Cl$_2$). >94% ee.

B. Intramolecular Diels-Alder Reaction of Malonate 45:

A solution of malonate 45 (22.8 mg, 0.069 mmol) in 1 mL toluene was heated in a sealed tube at 150° C. for 48 h. The mixture was concentrated and the residue purified by flash chromatography (petroleum ether/ether 11:1) to afford 16.5 mg (72%) of a product tentatively identified as hydrindane 46, as a colorless oil consisting of a mixture of 3 stereoisomers in a ratio of 49:44:7 ($^1$H NMR; integration of the methoxycarbonyl signals). $[\alpha]_D=+64.9$ (c 0.45, CH$_c$Cl$_2$). $^1$H and $^{13}$C NMR of the two major isomers: $^1$H NMR (500 MHz, CDCl$_3$) δ: 7.19–7.33 (m, 10 H), 5.81 (d, J=9.5 Hz, 1 H), 5.75 (ddd, J=10.0, 6.5, 2.7 Hz, 1 H), 5.57–5.65 (m, 2 H), 3.95 (d, J=5.0 Hz, 1 H), 3.81 (d, J=12.5 Hz, 1 H), 3.78 (s, 3 H), 3.73 (s, 3 H), 3.22–3.31 (m, 1 H), 3.09 (s, 3 H), 3.03 (s, 3 H), 2.81 (dd, J=13.3, 6.7 Hz, 1 H), 2.36–2.56 (m, 4 H), 2.02–2.18 (m, 3 H), 1.84 (dt, J=13.0, 4.6 Hz, 1 H), 1.78 (t, J=6.3 Hz, 1 H), 1.52–1.61 (m, 1 H), 1.44–1.49 (m, 1 H), 1.01–1.13 (m, 1 H), 1.05 (d, J=7.5 Hz, 3 H), 0.99 (d, J=7.0 Hz, 3 H). $^{13}$C NMR (75 MHz, CDCl$_3$) δ: 173.48, 172.62, 171.16, 171.02, 141.91, 138.48, 134.34, 134.16, 128.85, 128.71, 127.96, 127.77, 127.19, 126.83, 126.64, 66.08, 65.46, 57.73, 54.84, 52.73, 52.62, 51.86, 51.66, 44.72, 42.10, 41.58, 39.30, 38.56, 35.92, 32.57, 30.47, 30.39, 21.98, 21.46. The 3rd isomer was identified by its two $^1$H NMR signals for the malonate methyl groups at 3.74 (s, 3 H) and 3.10 (s, 3 H).

Examples 21A–B

Preparation of methyl (4E)-5-(1-Cyclohexen-1-yl)-2-methoxycarbonyl-2-(2-propenyl)-3-vinyl-4-pentenoate 47 and subsequent Diels-Alder reaction

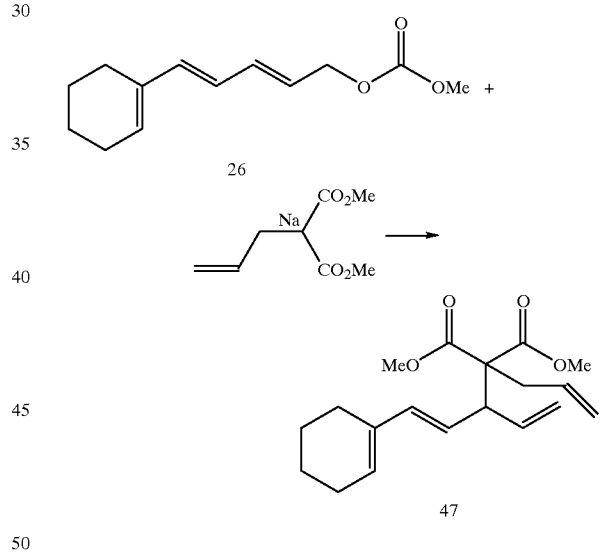

47

A. According to procedure B with Mo(CO)$_3$(EtCN)$_3$ (12.2 mg, 0.035 mmol) and ligand (R,R)-I (17.2 mg, 0.053 mmol) in 2 mL toluene and carbonate 26 (78.6 mg, 0.35 mmol), dimethyl allylmalonate (133.9 mg, 0.78 mmol) and sodium hydride (28.3 mg, 0.71 mmol) in 2 mL THF. The reaction mixture was heated at 90° C. for 2.5 h. Two isomers in ratio of 5:1 were obtained, according to $^1$H NMR spectroscopy (integration of the methoxycarbonyl signals) of the crude mixture. Purification by flash chromatography (petroleum ether/ether 12:1) afforded 79.9 mg (71%) of pure 47 as a colorless oil. $[\alpha]_D=-52.0$ (c 0.38, CH$_2$Cl$_2$). The ee could not be determined.

B. Intramolecular Diels-Alder reaction of malonate 47:

A solution of malonate 47 (15.0 mg, 0.047 mmol) in 2 mL toluene was heated in a sealed tube at 150° C. for 15 h. The mixture was concentrated and the residue purified by flash chromatography (petroleum ether/ether 12:1) to afford 14.5 mg (97%) of a product tentatively identified as tricycle 63, as a colorless oil consisting of a mixture of 4 stereoisomers in a ratio of 3:3:1:1 ($^1$H NMR; integration of the methoxycarbonyl signals). $[\alpha]_D$=−67.4 (c 0.44, $CH_2Cl_2$). $^1$H NMR (300 MHz, $CDCl_3$) δ: 4.95–5.77 (m, 4 H), 3.75, 3.74, 3.73, 3.71, 3.67, 3.65, 3.62, 3.60 (8s, 6 H), 2.68–3.07 (m, 1 H), 0.80–2.54 (m, 15 H). $^{13}$C NMR (75 MHz, $CDCl_3$) δ: 173.27, 172.96, 172.14, 171.89, 143.50, 141.57, 141.09, 137.32, 136.73, 135.97, 135.89, 135.39, 119.45, 119.28, 118.79, 118.63, 117.71, 117.53, 117.42, 63.85, 63.75, 54.92, 54.20, 53.96, 52.64, 52.63, 52.46, 52.10, 51.92, 47.49, 47.28, 42.91, 42.34, 40.35, 39.46, 39.22, 39.11, 39.00, 38.80, 38.67, 37.85, 37.23, 36.26, 36.16, 35.97, 35.16, 34.84, 34.79, 34.72, 34.30, 34.00, 29.69, 28.75, 27.12, 27.04, 25.94.

It is claimed:

1. A method of selective alkylation of a substrate having an allyl group bearing a leaving group at the allylic position, said method comprising reacting said substrate with an alkylating agent in the presence of a catalytic composition formed by contacting, in a suitable solvent, catalytic amounts of (i) a chiral ligand $L^1$, said ligand comprising (a) an axially chiral 1,1'-binaphthyl system, said system substituted at its 2 position and at its 2' position with a group X selected from —O— or —NR—, where R is hydrogen or lower alkyl, and, linked to each said group X, (b) a binding group $Cy_N$ comprising a heterocyclic group having a ring nitrogen atom effective to bind to a metal atom selected from the group consisting of molybdenum, tungsten, and chromium, wherein said heterocyclic group is optionally substituted with one or more groups selected from alkyl, alkenyl, aryl, aralkyl, alkoxy, aryloxy, acyl, acyloxy, amide, tertiary amine, nitro, or halogen, and may be fused to one or more additional rings; and (ii) a hexacoordinate complex of a metal selected from the group consisting of molybdenum (0), tungsten (0), and chromium (0), said hexacoordinate complex comprising ligands which are effective to form a stable complex with said metal atom and which are displaceable by ligand $L^1$ under the conditions of said contacting, under conditions effective to produce an alkylated product which is enriched in one of the possible isomeric products of such alkylation.

2. A method of selective alkylation of a substrate having an allyl group bearing a leaving group at the allylic position, said method comprising reacting said substrate with an alkylating agent in the presence of a catalytic composition formed by contacting, in a suitable solvent, catalytic amounts of (i) a chiral ligand $L^1$, said ligand comprising (a) a chiral component derived from a chiral diamine, diol, or amino alcohol, said component having first and second chiral carbon centers, each substituted with a group X selected from —O— or —NR—, where R is hydrogen or lower alkyl, the chiral centers are connected by a direct bond or by a chain of one to three atoms comprising linkages selected from alkyl (carbon-carbon), alkyl ether (carbon-oxygen), alkyl amino (carbon-nitrogen), or a combination thereof, and each chiral center is further substituted with groups $R^1$ and $R^2$, which are independently selected from the group consisting of aryl, heteroaryl, aralkyl, cycloalkyl, or heterocyclyl, or together form a carbocyclic or heterocyclic ring, and, linked to each said group X, (b) a binding group $Cy_N$ comprising a heterocyclic group having a ring nitrogen atom effective to bind to a metal atom selected from the group consisting of molybdenum, tungsten, and chromium, wherein said heterocyclic group is optionally substituted with one or more groups selected from alkyl, alkenyl, aryl, aralkyl, alkoxy, aryloxy, acyl, acyloxy, amide, tertiary amine, nitro, or halogen, and may be fused to one or more additional rings, and (ii) a hexacoordinate complex of a metal selected from the group consisting of molybdenum (0), tungsten (0), and chromium (0), said hexacoordinate complex comprising ligands which are effective to form a stable complex with said metal atom and which are displaceable by ligand $L^1$ under the conditions of said contacting, under conditions effective to produce an alkylated product which is enriched in one of the possible isomeric products of such alkylation.

3. The method of claim 2, wherein said alkylation is enantioselective.

4. The method of claim 3, wherein said alkylation produces an alkylated product having an enantiomeric excess greater than 85%.

5. The method of claim 2, wherein said metal atom is molybdenum.

6. The method of claim 2, wherein said ligands are selected from the group consisting of CO, cycloheptatriene, lower alkyl nitrile, and lower alkyl isonitrile.

7. The method of claim 2, wherein the mole percent of said catalytic composition with respect to said substrate is from about 0.5% to about 15%.

8. The method of claim 2, wherein said ligand $L_1$ has the structure

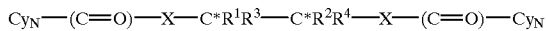

wherein said chiral centers are connected by a direct bond, $R^1$ and $R^2$ are as defined above, $R^3$ and $R^4$ are hydrogen, and binding groups $Cy_N$ are as defined above.

* * * * *